(12) United States Patent
Rade et al.

(10) Patent No.: US 8,454,952 B2
(45) Date of Patent: Jun. 4, 2013

(54) AUGMENTATION OF ENDOTHELIAL THROMBORESISTANCE

(75) Inventors: Jeffrey James Rade, Baltimore, MD (US); Navin Kumar Kapur, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 965 days.

(21) Appl. No.: 12/282,769

(22) PCT Filed: Mar. 13, 2007

(86) PCT No.: PCT/US2007/006191
§ 371 (c)(1),
(2), (4) Date: Dec. 30, 2008

(87) PCT Pub. No.: WO2007/108992
PCT Pub. Date: Sep. 27, 2007

(65) Prior Publication Data
US 2009/0186016 A1    Jul. 23, 2009

Related U.S. Application Data

(60) Provisional application No. 60/781,790, filed on Mar. 13, 2006.

(51) Int. Cl.
*A61K 39/395* (2006.01)
*C07K 16/22* (2006.01)

(52) U.S. Cl.
USPC .................................... 424/130.1; 530/387.1

(58) Field of Classification Search
None
See application file for complete search history.

(56) References Cited

U.S. PATENT DOCUMENTS

| 5,231,080 | A | 7/1993 | Scholkens |
| 5,536,723 | A | 7/1996 | Loscalzo et al. |
| 2002/0182659 | A1 | 12/2002 | Grainger et al. |
| 2004/0157861 | A1 * | 8/2004 | Scarborough et al. ........ 514/256 |
| 2005/0276802 | A1 | 12/2005 | Adams et al. |

FOREIGN PATENT DOCUMENTS
WO    03/013434    2/2003

OTHER PUBLICATIONS

Chaouat et al., The role of thrombosis in severe pulmonary hypertension. Eur. Respir. J. 9(2):356-363, Feb. 1996.*
European Search Report corresponding to Application No. EP 10 15 9682, dated Jul. 30, 2010.
Ohji et al., "Transforming Growth Factor Beta1 and Beta2 Induce Down-Modulation of Thrombomodulin in Human Umbilical Vein Endothelial Cells.", Thrombosis and Haemostasis, May 1995, pp. 812-818, vol. 73, No. 5.
Kim et al., "Early Loss of Thrombomodulin Expression Impairs Vein Graft Thromboresistance: Implications for Vein Graft Failure", Circulation Research, Feb. 8, 2002, pp. 205-212, vol. 90, No. 2.
Kuwahara et al., "Transforming Growth Factor-β Function Blocking Prevents Myocardial Fibrosis and Diastolic Dysfunction in Pressure-Overloaded Rats", Circulation, Jul. 2, 2002, pp. 130-135, vol. 106, No. 1.
Kapur et al., "Hemodynamic Modulation of Endocardial Thromboresistance" Circulation, Jan. 2007, pp. 67-75, vol. 115, No. 1.
Khan et al., "Fibrosis in heart disease: understanding the role of transforming growth factor-beta(1) in cardiomyopathy, valvular disease and arrhythmia", Immunology, May 2006, pp. 10-24, vol. 118, No. 1.
Kapur et al., "Transforming growth factor beta inhibition attenuates vein graft thrombosis", Circulation, Oct. 16, 2007, p. 134, vol. 116, No. 16, Supplement S, BIOSIS AN 2008:196026.
International Search Report, Sep. 2008.
T. Mitsui et al., "Imidapril, an Angiotensin-Converting Enzyme Inhibitor, Inhibits Thrombosis Via Reduction in Aortic Plasminogen Activator Inhibitor Type-1 Levels in Spontaneously Hypertensive Rats," Biological and Pharmaceutical Bulletin, Aug. 1999, vol. 22, No. 8, pp. 863-865.
Supplemental EPO Search Report, Aug. 5, 2009.

* cited by examiner

*Primary Examiner* — Ruixiang Li
(74) *Attorney, Agent, or Firm* — Banner & Witcoff, Ltd.

(57) ABSTRACT

Stretch-induced increased hemodynamic load adversely affects endothelial cell function and is an important contributor to thromboembolus formation in heart failure, valvular heart disease, atrial fibrillation, venous insufficiency, and pulmonary hypertension, and in thrombus occluded vein grafts. Local thrombus formation and thromboenbolic events can be reduced by inhibiting the TGF-beta signaling pathway or TGF-beta per se. Inhibitors can be administered to patients or veins (prior to interposition) at risk for thromboembolic events or local thrombus formation. Inhibitors can be applied to harvested veins to be used as arterial grafts.

23 Claims, 17 Drawing Sheets

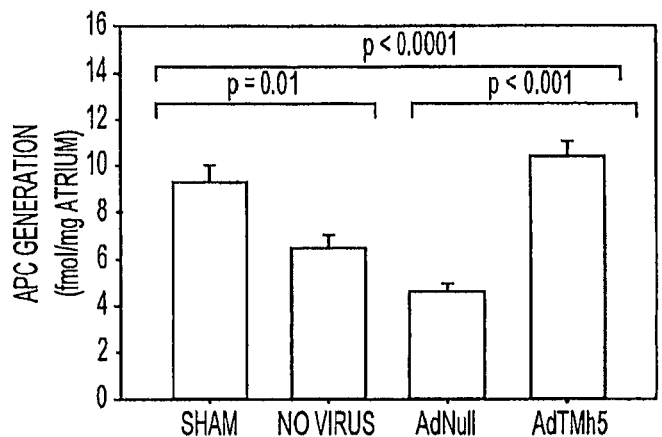
FIG. 4A
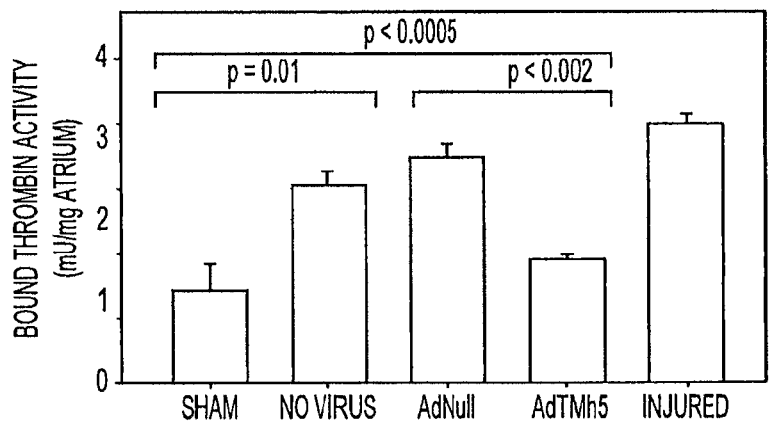
FIG. 4B
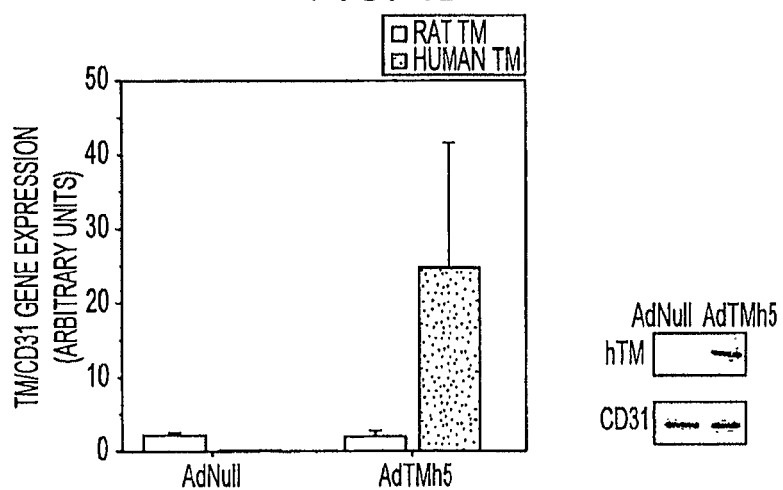
FIG. 4C
FIG. 4D

RIGHT ATRIAL LUMEN

AUGMENTATION OF ENDOTHELIAL THROMBORESISTANCE

This work leading to this invention was supported by grants from the US government, National Heart, Lung and Blood Institute grant HL-080142. The US government therefore retains certain rights in the invention.

TECHNICAL FIELD OF THE INVENTION

This invention is related to the area of endothelial cells. In particular, it relates to endothelial cells of the endocardium and blood vessels.

BACKGROUND OF THE INVENTION

Congestive heart failure is a growing public health problem affecting over 5 million people in the United States. Thromboembolic events, including stroke, are a major cause of morbidity and mortality in patients with heart failure.[1] The annual risk of a thromboembolic event with mild to moderate heart failure and sinus rhythm ranges from 1.5-2.5% and exceeds 5% in severe disease.[2,3] Thromboembolus formation in heart failure has historically been ascribed to blood stasis within the dilated cardiac chambers.[4] Stasis alone, however, cannot fully explain intracardiac thrombus formation as even patients with heart failure and preserved systolic function remain at increased risk for stroke compared to those without heart failure.[5] While recent evidence does suggest that heart failure may be associated with a mild degree of hypercoagulation[6], what has received relatively little attention and yet may be a significant contributor to intracardiac thrombus formation is the third arm of Virchow's triad-dysfunction of the endocardial endothelium.

Thrombomodulin (TM) is a 100 kD membrane glycoprotein that is a major regulator of vascular thromboresistance.[7] It is expressed in abundance by vascular endothelial cells, including those comprising the endocardium.[8] binds thrombin and renders it incapable of enzymatically cleaving fibrinogen or activating cellular thrombin receptors but enables the activation of circulating protein C. Activated protein C (APC) degrades factors Va and XIIIa of the coagulation cascade, potently inhibiting further thrombin generation. Deletion of the TM gene causes lethal thrombosis in mice and the acquired loss of TM in humans is thought to contribute to the thrombotic manifestations of bacterial sepsis, radiation enteropathy and coronary atherosclerosis.[9-11]

Autologous vein grafts are the most frequently used conduits for coronary and peripheral arterial bypass surgery. Compared with arterial grafts, vein grafts suffer a significantly higher failure rate that limits their clinical efficacy. One-and 12-month failure rates for coronary bypass vein grafts approach 12% and 20%, respectively, and are predominantly due to occlusive thrombosis. Late vein graft failure is due mainly to neointimal hyperplasia and accelerated atherosclerosis. Although surgical trauma and technical factors have often been invoked as possible causes of early graft failure, little is known about changes that may occur to the graft endothelium that might predispose to thrombosis. Thrombomodulin is down-regulated in vein grafts. Reduction in its expression facilitates local thrombin generation that predisposes to thrombotic graft occulusion.[13] Moreover, thrombomodulin protein and gene expression highly correlate with changes in wall tension, such as occur when veins grafts are exposed to arterial pressure.[12]

We recently identified pressure-induced vascular stretch as a novel and potent inhibitory stimulus for endothelial TM expression.[12] This was first observed in rabbit vein segments implanted into the arterial circulation where TM protein expression decreased by 95% and resulted in increased local thrombin generation and microthrombus formation.[13]

There is a continuing need in the art to decrease stroke risk in patients with congestive heart failure, valvular heart disease, and atrial fibrillation without subjecting them to the risks of systemic anticoagulation. There is a continuing need in the art to improve the success rate of vein grafts for arterial bypass surgery.

SUMMARY OF THE INVENTION

According to one embodiment of the invention the risk of a local thrombosis or thromboembolic event in a patient with congestive heart failure is reduced by administering to the patient an effective amount of an agent. The agent is selected from the group consisting of: an ACE inhibitor, an angiotensin receptor blocker, an anti-TGF-β antibody, a TGF-β anti-sense molecule, a vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptors.

According to another embodiment of the invention the risk of a local thrombosis or thromboembolic event in a patient with valvular heart disease is reduced by administering to the patient an effective amount of an agent. The agent is selected from the group consisting of: an ACE inhibitor, an angiotensin receptor blocker, an anti-TGF-β antibody, a TGF-β anti-sense molecule, a vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptors.

According to yet another embodiment of the invention the risk of a local thrombosis or thromboembolic event in a patient with atrial fibrillation is reduced by administering to the patient an effective amount of an agent. The agent is selected from the group consisting of: an ACE inhibitor, an angiotensin receptor blocker, an anti-TGF-β antibody, a TGF-β anti-sense molecule, a vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptors.

According to still another embodiment of the invention the risk of a local thrombosis or thromboembolic event in a patient with venous insufficiency is reduced by administering to the patient an effective amount of an agent. The agent is selected from the group consisting of: an ACE inhibitor, an angiotensin receptor blocker, an anti-TGF-β antibody, a TGF-β anti-sense molecule, a vector encoding a TGF-β anti-sense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptors.

According to an additional embodiment of the invention the risk of a local thrombosis or thromboembolic event in a patient with pulmonary hypertension is reduced by administering to the patient an effective amount of an agent. The agent is selected from the group consisting of: an ACE inhibitor, an angiotensin receptor blocker, an anti-TGF-β antibody, a TGF-β anti-sense molecule, a vector encoding a TGF-β anti-sense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptors.

Another aspect of the invention is a method of treating a harvested vein to reduce the risk of a local thrombosis when grafted into an artery. The harvested vein is treated with an effective amount of an agent selected from the group consisting of: an ACE inhibitor, an angiotensin receptor blocker, an anti-TGF-β antibody, a lentivirus vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptor. The incidence of vein graft failure due to local thrombosis is thereby reduced.

According to another aspect of the invention a method is provided for treating a patient to reduce the risk of a local thrombosis in a vein grafted into an artery. An effective amount of an agent is administered to a patient prior to, during, or subsequent to receiving a vein graft into an artery. The agent is selected from the group consisting of: an ACE inhibitor, an angiotensin receptor blocker, an anti-TGF-β antibody, a lentivirus vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptor. The risk or incidence of vein graft failure due to local thrombosis is thereby reduced.

Another aspect of the invention provides a method of assessing vein graft failure due to local thrombosis. A harvested vein is treated with an effective amount of an agent selected from the group consisting of: an ACE inhibitor, an angiotensin receptor blocker, an anti-TGF-β antibody, a TGF-β anti-sense molecule, a vector encoding a TGF-β anti-sense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptor. The patency of the treated vein is monitored within 180 days after it has been grafted in an artery of a patient to determine early graft occlusion due to thrombus formation.

Another embodiment of the invention is a method of assessing vein graft failure due to local thrombosis. An effective amount of an agent is administered to a patient prior to, during, or subsequent to receiving a vein graft into an artery. The agent is selected from the group consisting of: an ACE inhibitor, an angiotensin receptor blocker, an anti-TGF-β antibody, a TGF-β antisense molecule, a vector encoding a TGF-β antisense molecule, a silencing RNA which silences TGF-β, a TGF-β receptor anti-sense molecule, a vector encoding a TGF-β receptor antisense molecule, a vector expressing Smad6 or Smad7, a Smad2 or Smad4 antisense molecule, a vector encoding a Smad2 or Smad4 antisense molecule, and a silencing RNA which silences TGF-β receptor. The risk or incidence of vein graft failure due to local thrombosis is thereby reduced. The patency of the treated vein is monitored within 180 days after it has been grafted in an artery of the patient to determine early graft occlusion due to thrombus formation.

These and other embodiments which will be apparent to those of skill in the art upon reading the specification provide the art with prophylactic treatment and assessment modes to minimize pathological thromboses.

BRIEF DESCRIPTION OF THE DRAWINGS

FIG. 1A, Left ventricular systolic and diastolic pressures measured by cardiac puncture (n=8/group). FIG. 1B, Left atrial (LA) diameter, left ventricular diastolic posterior wall thickness (LVPWd) and left ventricular internal diastolic diameter (LVIDd) as measured by echocardiography (n=8/group). FIG. 1C, Serum levels of atrial natriuretic peptide (ANP; n=6-8/group), brain natriuretic peptide (BNP; n=7-8/group), angiotensin II (AT II; n=7-8/group) and tumor necrosis factor-α (TNF-α; n=3-4/group).

FIG. 2A, TM gene expression, normalized to CD31, was determined by quantitative PCR of tissue extracts obtained from the left atrium (n=10/group), left ventricle (n=10/group) and the distal aorta (n=8/group) of banded and sham rats 96 hours after surgery. FIG. 2B, TM protein expression, normalized to CD31, was determined by densitometric analysis of Western blots of left atrial tissue extracts obtained from banded and sham rats (n=4-5/group) 96 hours after surgery. The right panel depicts a representative Western blot. FIG. 2C, Histologic sections of left atrial tissue obtained from sham and banded rats 96 hours after surgery stained with an anti-mouse TM antibody showing decreased endocardial TM protein expression.

FIGS. 4A-4D. Effects of TM expression on endocardial thromboresistance. FIG. 4A, APC generating capacity was assessed 96 hours after surgery in the left atria of sham-operated and banded rats (n=10/group) as well as in banded rats whose left atria were transduced with either AdNull or AdTMh5 5 days prior to surgical banding (n-S/group). FIG. 4B, Bound thrombin activity, proportional to microthrombus burden, was measured 96 hours after surgery in the left atria of sham-operated and banded rats (n=10/group) as well as in banded rats whose left atria were transduced with either AdNull or AdTMh5 5 days prior to surgical banding (n—S/group). FIG. 4C, Rat left atria were transduced with either AdNull or AdTMh5, an adenovirus vector expressing human TM. Three days after transduction, atrial tissue was subjected to Western blot analysis using antibodies that recognize the human isoform of TM and rat CD31. The depicted blot is representative of n=3 experiments. FIG. 4D, Rat left atria were transduced with either AdNull (n=5) or AdTMh5 (n=8) five days prior to surgical banding. 96 hours after banding, TM gene expression was determined in atrial tissue by quantitative PCR using species-specific probes and primers.

FIG. 5A, Human atrial endothelial cells were plated on collagen-coated Bioflex plates and subjected to increasing amounts of cyclic stretch at 1 Hz for 24 hours. TM gene expression, normalized to rRNA, was determined by quantitative PCR (n=5/group). FIG. 5B, Human atrial endocardial cells were plated on stationary filters submerged in the media of human cardiac fibroblasts subjected to increasing amounts of cyclic stretch at 1 Hz for 24 hours. TM gene expression, normalized to rRNA, was determined by quantitative PCR (n=4/group).

FIG. 6A, Human cardiac fibroblasts were subjected to increasing amounts of cyclic stretch for 24 hours. TGF-β gene expression, normalized to rRNA, was determined by quantitative PCR (n=6/group). FIG. 6B, Human atrial endocardial cells were incubated with increasing concentrations of recombinant human TGF-$β_1$ for 24 hours. TM gene expression, normalized to rRNA, was determined by quantitative PCR (n=4/group). FIG. 6C, Human atrial endocardial cells were plated on stationary filters submerged in the media of human cardiac fibroblasts subjected to 10% cyclic stretch for 24 hours in the presence of 0.5 μg/mL of neutralizing TGF-β or isotype control antibodies. TM gene expression, normalized to rRNA, was determined by quantitative PCR (n=4/group).

FIG. 7A, TGF-β gene expression, normalized to rRNA, was determined by quantitative PCR of tissue extracts obtained from the left atrium (n=10/group), left ventricle (n=8/group) and in the distal aorta (n=8/group) of banded and sham operated rats 96 hours after surgery. FIG. 7B, Sham and banded atria were immunostained for TGF-β activation with an antibody recognizing the cleaved latency associated peptide (LAP). TGF-β activation localized to fibroblast-appearing cells in the subendocardial space abundantly expressing rat prolyl 4-hydroxylase (rPH). FIG. 7C, Rats were administered 1 mg/kg of either a neutralizing an anti-TGF-β or isotype control antibody 24 hours prior to aortic banding and a second dose of 0.5 mg/kg 48 hours post-operatively. TM gene expression, normalized to CD31, was determined 96 hours after surgery by quantitative PCR of left atrial tissue extracts and compared to sham operated controls (n=6/group).

DETAILED DESCRIPTION OF THE INVENTION

The inventors have developed various methods to reduce the risk/incidence of local thrombus formation and thromboembolic events. In particular, the methods reduce the incidence (and therefore prevent some) local thrombus formation in blood vessels and/or cardiac chambers exposed to pathologic pressure-induced vascular stretch. The methods are useful for treating patients with congestive heart failure, valvular heart disease, atrial fibrillation, venous insufficiency, and pulmonary hypertension, each of which is characterized by local thrombus formation and abnormal pressure-induced stretch. Veins grafted into arteries are subject to pressure-induced stretch, due to the pressure differences between veins and arteries. The inventors have identified an important role of paracrine effects of transforming growth factory (TGF-β in regulating endothelial cell thrombomodulin ("TM") expression.

The major findings upon which the invention is based include: 1) acute elevations in filling pressure adversely affect atrial endothelial cell TM expression; 2) downregulation of endothelial TM expression impairs local protein C activation and contributes to local thrombin generation; 3) endothelial TM expression is negatively regulated during acute pressure overload by the paracrine effects of TGF-β secreted by connective tissue in response to pressure-induced chamber stretch.

It has long been recognized that patients with heart failure develop intracardiac thrombi that cause cerebral, pulmonary and peripheral arterial thromboembolization. Thrombus formation has traditionally been viewed as a consequence of blood stasis resulting from impaired ventricular function. If the presence of atrial fibrillation is excluded, however, the degree of left ventricular dysfunction only weakly correlates with thromboembolic risk.[3] This suggests that factors other than stasis contribute to intracardiac thrombus formation in patients with heart failure, the overwhelming majority of who remain in sinus rhythm. We demonstrate below that elevated cardiac filling pressures can adversely affect endocardial function and predispose to intracardiac thrombus formation independent of blood stasis.

Figure 9:
FIG. 9. Histologic section of a human right atrial appendage immunostained with an anti-human TM antibody demonstrating endocardial TM protein expression.

TM is but one of several anticoagulant molecules expressed by endothelial cells that protect against pathologic thrombosis. The level of TM expression varies among endothelial cell types and therefore its relative contribution to vascular thromboresistance may differ between vascular beds.[22,23] Several elements of the present study suggest that TM is a critical contributor to endothelial, and in particular endocardial endothelial thromboresistance. The first is that TM is expressed in abundance by the endocardial endothelium. In addition to the rat, we have also found that in situ endocardial endothelial TM expression is also robust in the rabbit[8] and in humans (FIG. 9). Second, increased local thrombin generation in our model was proportional to the downregulation of TM and occurred despite changes in the expression of other anticoagulant molecules that would be expected to inhibit thrombus formation. Third and most importantly, targeted restoration of TM expression using adenovirus-mediated gene transfer effectively reduced local thrombin generation.

In prior studies using rabbit vein grafts, we identified pressure-induced vascular stretch as a novel and potent negative regulator of in vivo TM expression. The present study extends these findings by providing evidence of a second, and uniquely important, vascular bed in which stretch modulates TM expression and by identifying paracrine release of TGF-β as the critical molecular mediator. TGF-β is a multifunctional dimeric polypeptide growth factor that is involved in a diverse array of biological processes including embryogenesis, tumor growth, wound healing and tissue remodeling.[24] It is intimately involved in the adaptive response of cardiac and vascular tissue to pressure overload. In systolic heart failure for example, TGF-β expression is known to be markedly increased in cardiac myocytes and fibroblasts where it is a recognized autocrine and paracrine mediator of hypertrophy and fibrosis.[25]

In the model of acute pressure overload used in the examples below a marked increase in local TGF-β expression was observed in the left atrium but not in the left ventricle and appeared to originate predominantly from cardiac fibroblasts. This was likely due to the relatively greater hemodynamic load imposed upon the atrium and explains why endocardial TM expression in the ventricle did not change. A recognized limitation of this model is the absence of ventricular remodeling and systolic dysfunction common to most chronic heart failure models. While the model most replicates features of diastolic heart failure, it was precisely the absence of systolic dysfunction that obviated potential confounding effects of blood stasis on intracardiac thrombin generation. In models of chronic systolic dysfunction, TGF-β expression is increased in ventricular tissue[26] and it is reasonable to predict that TM expression in the overlying endocardium would also be reduced. Adaptive responses, however, may complicate this issue as there is evidence that myocardial TGF-β expression may vary according to the etiology of heart failure and may change over time as heart failure progresses.[27,28] This raises the possibility that the risk and chamber origin of thrombus formation may change over time and may be greater for different types of heart failure.

Extremely little is known about the molecular mechanism by which TGF-β regulates TM expression in endothelial cells. TGF-β signal transduction is initiated via binding to specific serine/threonine type I and type II receptor complexes located on the endothelial cell surface.[29] Receptor engagement causes the phosphorylation of several intracellular effector molecules known as Smads. While most of the Smad proteins (such as Smad2 and Smad4) positively regulate TGF-β signal transduction, Smad6 and Smad7 are known to exert inhibitory effects. One publication that investigates the mechanism of TM modulation by TGF-β, reported that antisense inhibition of Smad7 potentiated the effects of TGF-β while antisense inhibition of a splice variant of Smad6, known as Smad6s, unexpectedly blunted the downregulation of TM in human umbilical endothelial cells by TGF-β.[30] As Smad6 and Smad7 are differentially expressed in the endothelium of normal and atherosclerotic arteries[30] they may be able to differentially modulate the paracrine effects of TGF-β on TM expression in various vascular beds and disease states.

In addition to heart failure, our findings may have implications for understanding the thrombogenic potential of other forms of cardiovascular disease, such as atrial fibrillation. Thrombus formation in atrial fibrillation is also primarily ascribed to blood stasis in a non-contracting left atrial appendage. However, it is well known that atrial fibrillation in patients with structurally normal hearts, i.e., "lone atrial fibrillation," is associated with a relatively small risk (<0.5% per year) of thromboembolic stroke compared to atrial fibrillation that occurs in the setting of hypertension, heart failure or valvular heart disease (5-12% per year).[31] As these latter conditions are all characterized by pressure-induced atrial distension, it is possible that endothelial endocardial dysfunction and altered TM expression may contribute substantially to the thromboembolic risk in these patients. This concept is supported by data from a rat model of atrial fibrillation where atrial TM expression decreased by 35% following 8 hours of rapid atrial pacing.[32] Interestingly, the left atrial pressure in this model triples during pacing 33, raising the possibility that the effects on TM expression were primarily the result of hemodynamic rather than electrical influences.

Agents which can be used to prophylactically treat and reduce the incidence of thrombus, microthrombus, or thromboembolism are any which inhibit TGF-beta expression or binding to its receptor, or any of the downstream effectors in its signaling pathway. These include but are not limited to ACE inhibitors (e.g., Captopril (Capoten®), Enalapril (Vasotec®/Renitec®), Ramipril (Altace®/Tritace®/Ramace®/Ramiwin®), Quin april (Accupril®), Perindopril (Coversyl®), Lisinopril (Lisodur®/Lopril®/Prnivil®/Zestril®), Benazepril (Lotensin®), Fosinopril (Monopril®)), angiotensin receptor blockers (e.g., Ribeiro AB. Angiotensin II antagonists—therapeutic benefits spanning the cardiovascular disease continuum from hypertension to heart failure and diabetic nephropathy. Curr Med Res Opin. 2006 January; 22(1):1-16; Volpe M, et al. Angiotensin II-receptor antagonist in the treatment of hypertension. Curr Hypertens Rep. 2005 August; 7(4):287-93; Cruden N L, Newby D E. Angiotensin antagonism in patients with heart failure: ACE inhibitors, angiotensin receptor antagonists or both? Am J Cardiovasc Drugs. 2004; 4(6):345-53.) anti-TGF-β antibodies (see, e.g., C L Arteaga Anti-transforming growth factor (TGF)-beta antibodies inhibit breast cancer cell tumorigenicity and increase mouse spleen natural killer cell activity. Implications for a possible role of tumor cell/host TGF-beta interactions in human breast cancer progression, J Clin Invest. 1993 December; 92(6): 2569-2576), TGF-β anti-sense molecules (see, e.g., Fakhrai H, Phase I clinical trial of a TGF-beta antisense-modified tumor cell vaccine in patients with advanced glioma, Cancer Gene Ther. 2006 December; 13(12):1052-60. Epub 2006 Jul. 7.), vectors encoding a TGF-β antisense molecule, silencing RNAs which silence TGF-β (see, e.g., Liu F, Inhibition of TGF-beta1 expression in human peritoneal mesothelial cells by pcDU6 vector-mediated TGF-beta1 shRNA. Nephrology, 2006 February; 11(1):23-8.), TGF-β receptor anti-sense molecules, vectors encoding a TGF-β receptor antisense molecule, vectors expressing Smad6 or Smad7 (see, e.g., Nakao A, et al., Identification of Smad7, a TGFbeta-inducible antagonist of TGF-beta signaling. Nature. 1997 Oct. 9; 389(6651):631-5.), Smad2 or Smad4 antisense molecules, vectors encoding a Smad2 or Smad4 antisense molecule (see, e.g., Kretschrner A, et al., Differential regulation of TGF-beta signaling through Smad2, Smad3 and Smad4. Oncogene. 2003 Oct. 2; 22(43):6748-63.), and silencing RNA which silences TGF-β receptor (see, e.g., Jazag A, et al., Single small-interfering RNA expression vector for silencing multiple transforming growth factor-beta pathway components. Nucleic Acids Res. 2005 Aug. 19; 33(15):e131). Additional useful agents include those which specifically inhibit Smad2 and Smad4 phosphorylation. Also useful are decoy oligonucleotides which bind to the same nucleic acid binding sites as Smad2 and Smad4 (see, e.g., Massague J, et al., Genes Dev. 2005 Dec. 1; 19(23):2783-810.). These agents are known in the art.

Monitoring for occlusions of vein grafts can be done by any method known in the art. Preferably the method will be non-invasive. One particular method which can be used is computerized axial tomographic arteriography (CT angiogram). Such a method will detect whether thrombi have formed in the vein graft and prevented flow through the vein graft. Typically when such occlusions occur, there is no flow from anastomosis to anastomosis, i.e., from end to end of the vein graft. The vein grafts of the invention may be, for example, grafts into the coronary artery or into a peripheral artery.

Because occlusions of vein grafts occur early in the life of a vein graft, e.g., in the first 6 to 12 months, one should monitor early. Monitoring should be done before 1 year, before 9 months, before 6 months, before 5 months, before 4 months, or before 3 months. Monitoring can be done immediately after grafting, or after 7 days, after 14 days, or after 30 days. The appropriate time window may depend on the patient's general condition and the condition of the graft.

Vectors according to the present invention for delivering molecules which are antisense or sense, may be either viral or non-viral. Suitable viral vectors include lentivirus, adenovirus, adeno-associated virus, retrovirus, and herpes virus vectors. Suitable non-viral vectors include liposomes and DNA complexes, for example polycationic complexes.

More preferably the TGF-beta antagonist is a human or humanized monoclonal antibody that blocks TGF-beta binding to its receptor (or fragments thereof such as F(ab), fragments, Fv fragments, single chain antibodies and other forms of "antibodies" that retain the ability to bind to TGF-beta). Most preferred, the monoclonal antibody is a human or humanized form of the murine monoclonal antibody obtained from hybridoma ID 11.16 (ATCC Accession No. HB 9849).

TGF-beta is a disulfide linked dimer that is synthesized as a preproprotein of about 400 amino acids (aa) which is cleaved prior to secretion to produce mature TGF-beta. The N-terminal cleavage fragment, known as the "latency-associated peptide" (LAP), may remain noncovalently bound to the dimer, thereby inactivating TGF-beta. TGF-beta, isolated in vivo, is found predominantly in this inactive "latent" form associated with LAP. Latent TGF-beta complex may be activated in several ways, for example, by binding to cell surface receptors called the cation-independent mannose-6-phosphate/insulin-like growth factor II receptor. Binding occurs through mannose-6-phosphate residues attached at glycosylation sites within LAP. Upon binding to the receptor, TGF-beta is released in its mature form. Mature, active TGF-beta is then free to bind to its receptor and exert its biological functions. The major TGF-beta-binding domain in the type II TGF-beta receptor has been mapped to a 19 amino acid sequence (Demetriou et al. (1996) J. Biol. Chem., 271:12755).

As used herein, "TGF-beta" refers to all isoforms of TGF-beta. There are currently 5 known isoforms of TGF-beta (1-5), all of which are homologous (60-80% identity) and all of which form homodimers of about 25 kD, and act upon common TGF-beta cellular receptors (Types I, II, and III). The genetic and molecular biology of TGF-beta is well known in the art (see, for example, Roberts, 1998 Miner. Electrolyt and Metab. 24:111; Wrana, 1998, Miner. Electroly and Metab 24:120-130 and 174-180, WO 98/07849).

As used herein, a "TGF-beta antagonist" is any molecule that is able to decrease the amount or activity of TGF-beta, either within a cell or within a physiological system. Preferably, the TGF-beta antagonist acts to decrease the amount or activity of a mammalian TGF-beta1, 2, or 3. For example, a TGF-beta antagonist may be a molecule which inhibits expression of TGF-beta at the level of transcription, translation, processing, or transport; it may affect the stability of TGF-beta or conversion of the precursor molecule to the active, mature form; it may affect the ability of TGF-beta to bind to one or more cellular receptors (e.g., Type I, II or III); or it may interfere with TGF-beta signaling. The molecule may be, e.g., a peptide, a protein, an oligonucleotide, a nucleic acid, or a small chemical entity.

A variety of TGF-beta antagonists and methods for their production are well known in the art and many more are currently under development (see for example, Dennis & Demetriou, 1998). The specific TGF-beta antagonist employed is not a limiting feature; any effective TGF-beta antagonist as defined herein may be useful in the methods and compositions of this invention. Preferably, the TGF-beta antagonist is a TGF-beta1, TGF-beta2, or TGF-beta3 antagonist. Most preferably the antagonist is a TGF-beta1 antagonist.

Examples of TGF-beta antagonists include, but are not limited to: monoclonal and polyclonal antibodies directed against one or more isoforms of TGF-beta (Dasch, et al., 1996,U.S. Pat. No. 5,571,714; Thompson et al., 1997 WO/97/13844 and & 2000, WO00/66631); TGF-beta receptors or antibodies directed against TGF-beta receptors (Segarini et al., 1997, U.S. Pat. No. 5,693,607; Lin et al., 1999a, U.S. Pat. No. 6,001,969; Lin et al., 1999b, U.S. Pat. No. 6,008,011; Lin et al., 2000, US 6010872; Iwata et al., 1992, WO 92/00330; Lin et al., 1993WO 93/09228; Ruoslahti et al., 1995, WO 95/10610; and Gotwals et al., 1998, WO 98/48024); latency associated peptide (Levinson et al., 1991, WO 91/08291); large latent TGF-beta (Heldin et al., 1994, WO 94/09812); fetuin (Dennis and Demetriou, 1998, U.S. Pat. No. 5,821,227); decorin and other proteoglycans such as biglycan, fibromodulin, lumican and endoglin (Ruoslahti and Yamaguchi, 1996, U.S. Pat. No. 5,583,103; Ruoslahti; et al., 1997, U.S. Pat. No. 5,654,270; Ruoslahti et al., 1998, U.S. Pat. No. 5,705,609; Ruoslahti et al., 1998, U.S. Pat. No. 5,726,149; Border, 1998, U.S. Pat. No. 5,824,655; Letarte et al., 1998 U.S. Pat. No. 5,830,847; Letarte et al., 2000, U.S. Pat. No. 6,015,693; Border and Ruoslahti, 1991, US WO 91/04748; Ruoslahti and Yamaguchi, 1991, U.S. Pat. No. 5,583,103; Ruoslahti et al., 1993, WO 93/09800; and Letarte et al., 1994, WO 94/10187); somatostatin (Culler and Kasprzyk, 1998, WO 98/08529); mannose-6-phosphate or mannose-1-phosphate (Ferguson, 1996, U.S. Pat. No. 5,520,926); prolactin (McPherson and Richards, 1997, WO 97/40848); insulin-like growth factor II (Jeffrey and Gosiewska, 1998, WO 98/17304); IP-10 (Luster and Leder, 1997, WO 97/00691); arg-gly-asp containing peptides (Pfeffer, 1999, U.S. Pat. No. 5,958,411; Ruoslahti and Border, 1993, WO 93/10808); extracts of plants, fungi and bacteria (Aoki et al., 1993, EU 813875; Mayumi et al., 1996, JP 8119984; and Matsunaga et al., 1997, U.S. Pat. No. 5,693,610); antisense oligonucleotides (Chung, 1997 U.S. Pat. No. 5,683,988; Fakhrai et al., 1998, U.S. Pat. No. 5,772,995; Dzau, 1998, U.S. Pat. No. 5,821,234; Dzau, 1999, U.S. Pat. No. 5,869,462; and Schlingensiepen et al, 1994, WO 94/25588); proteins involved in TGF-beta signaling, including Smads and MADs (Okazaki and Kitamura, 1998, EP 874046; Donahoe and Wang, 1997, WO 97/31020; Goldstein, 1997, WO 97/38729; Matsumoto and Irie, 1998, WO 98/03663; Ni et al., 1998, WO 98/07735; Wrana et al., 1998, WO 98/07849; Gimeno and Falb, 1998, WO 98/45467; Nakao et al., 1998, WO 98/53068; Verschueren et al., 1998, WO 98/55512; Miyazono and Kawabata, 1998, WO 98/56913; Whitman and Chen, 1998, WO 98/53830; Grinnell et al., 1999, WO 99/50296; Falb, 1998, U.S. Pat. No. 5,834,248; Falb and Gimeno, 1998, U.S. Pat. No. 5,807,708; and Gimeno and Falb, 1999, U.S. Pat. No. 5,948,639; Ski and Sno (Vogel, 1999, Science 286:665; and Stroschein et al., 1999, Science 286:771-774); and any mutants, fragments or derivatives of the above-identified molecules that retain the ability to inhibit the activity of TGF-beta.

The TGF-beta antagonist may be a human or humanized monoclonal antibody that blocks TGF-beta binding to its receptor, or fragments thereof such as F(ab), fragments, Fv fragments, single chain antibodies and other forms of "antibodies" that retain the ability to bind to TGF-beta. In one embodiment, the TGF-beta antagonist is a human antibody produced by phage display (Thompson et al., 2000, WO 00/66631). In a more preferred embodiment, the monoclonal antibody is a human or humanized form of the murine monoclonal antibody obtained from hybridoma 1D11.16 (ATCC Accession No. HB 9849, as described in Dasch, et al., 1996, 1998a, and 1998b).

Mutants, variants, derivatives, and analogues of the aforementioned TGF-beta antagonist may also be useful in the methods of this invention. As used herein, "mutants, variants, derivatives and analogues" refer to molecules with similar shape or structure to the parent compound and that retain the ability to act as TGF-beta antagonists. For example, any of the TGF-beta antagonists disclosed herein may be crystallized, and useful analogues may be rationally designed based on the coordinates responsible for the shape of the active site(s). Alternatively, the ordinarily skilled artisan may, without undue experimentation, modify the functional groups of a known antagonist and screen such modified molecules for increased activity, half-life, bioavailability, or other desirable characteristics. Where the TGF-beta antagonist is a polypeptide, fragments and modifications of the polypeptide may be produced to increase the ease of delivery, activity, half-life, etc (for example, humanized antibodies or functional antibody fragments, as discussed above). Given the level of skill in the art of synthetic and recombinant polypeptide production, such modifications may be achieved without undue experimentation.

As used herein, a "pharmaceutically effective amount" is an amount effective to achieve the desired physiological result in a subject. Specifically, a pharmaceutically effective amount of a TGF-beta antagonist is an amount sufficient to decrease the quantity or activity of TGF-beta for a period of time sufficient to reduce the risk or incidence of thrombosis or thromboembolic event. The effective amount may vary depending on the specific TGF-beta antagonist selected, and is also dependent on a variety of factors and conditions related to the subject to be treated and the severity of the disorder (for example, the age, weight and health of the patient as well as dose response curves and toxicity data). The determination of a pharmaceutically effective amount for a given agent is well within the ability of those skilled in the art.

"Administration" to a patient is not limited to any particular delivery system and may include, without limitation, parenteral (including subcutaneous, intravenous, intramedullary, intraarticular, intramuscular, or intraperitoneal injection) rectal, topical, transdermal or oral (for example, in capsules, suspensions or tablets). Administration to a patient may occur in a single dose or in repeat administrations, and in any of a variety of physiologically acceptable salt forms, and/or with an acceptable pharmaceutical carrier and/or additive as part of a pharmaceutical composition (described earlier). Once again, physiologically acceptable salt forms and standard pharmaceutical formulation techniques are well known to persons skilled in the art (see, for example, Remington's Pharmaceutical Sciences, Mack Publishing Co.). Administration of a TGF-beta antagonist to a host individual may also be by means of gene transfer, wherein a nucleic acid sequence encoding the antagonist is administered to the patient (host) in vivo or to cells in vitro, which are then introduced into the patient, and the antagonist is thereafter produced by in situ expression of the product encoded by the nucleic acid sequence. Methods for gene therapy to deliver TGF-beta antagonists are also well known to those of skill in the art (see, for example, WO 96/25178). Treatment of a vein graft patient with a TGF-beta antagonist may be before, during, or after the graft is implanted. Alternatively, treatments may be performed directly on the graft itself, while outside the body. Vein treatments can, for example, be performed by soaking the graft in a solution comprising the TGF-antagonist.

The present invention may also employ a vector suitable for expression of a TGF-beta receptor or binding partner, preferably a soluble receptor or binding partner. More preferably, administration of a soluble TGF-beta antagonist is effected by gene transfer using a vector comprising cDNA encoding the soluble antagonist, most preferably cDNA encoding the extracellular domain of TGF-beta type II (rsTGFBIIR) or type III receptor (rsTGFBIIIR), which vector is administered, preferably topically, to a donor organ to cause in situ expression of the soluble TGF-beta antagonist in cells of the organ transfected with the vector. Such in situ expression inhibits the activity of TGF-beta and curbs TGF-beta-mediated fibrogenesis. Any suitable vector may be used. Preferred vectors include adenovirus, lentivirus, Epstein Barr virus (EBV), adeno associated virus (AAV), and retroviral vectors that have been developed for the purpose of gene transfer. See, e.g., Souza and Armentano, 1999, Biotechniques, 26:502-508. Other, non-vector methods of gene transfer may also be used, for example, lipid/DNA complexes, protein/DNA conjugates, naked DNA transfer methods, and the like. Antisense to a TGF-beta receptor may also be administered. See, e.g., Lenferink A E, Magoon J, Pepin M C, Guimond A, O'Connor-McCourt M D. Expression of TGF-beta type II receptor antisense RNA impairs TGF-beta signaling in vitro and promotes mammary gland differentiation in vivo. Int J. Cancer. 2003 Dec. 20; 107(6):919-28.

Additional suitable TGF-beta antagonists developed for delivery via adenoviral gene transfer include, but are not limited to: a chimeric cDNA encoding an extracellular domain of the TGF-beta type II Receptor fused to the Ig Fc domain (Isaka et al., 1999, Kidney Int., 55:465-475), adenovirus gene transfer vector of a dominant-negative mutant of TGF-beta type II Receptor (Zhao et al, 1998, Mech. Dev., 72:89-100.), and an adenovirus gene transfer vector for decorin, a TGF-beta binding proteoglycan (Zhao et al., 1999, Am. J. Physiol., 277:L412-L422. Adenoviral-mediated gene transfer is very high efficiency compared to other gene delivering modalities. However, in vivo gene transfer using adenoviral vectors as a therapeutic modality has been limited by the host immune response that induces inflammation, limits the amount and duration of transgene expression, and prevents effective re-transfection.

The above disclosure generally describes the present invention. All references disclosed herein are expressly incorporated by reference. A more complete understanding can be obtained by reference to the following specific examples which are provided herein for purposes of illustration only, and are not intended to limit the scope of the invention.

EXAMPLE 1

We hypothesized that pressure-induced chamber stretch might also negatively regulate endocardial TM expression and contribute to intracardiac thrombus formation during heart failure. To explore this, we characterized endocardial TM expression and function in a rat model of acute pressure overload. We then used adenovirus-mediated gene transfer to determine the relationship between thrombomodulin function and endocardial thromboresistance and identified an important role of paracrine effects of transforming growth factor-β (TGF-β) in regulating endocardial TM expression.
Methods Rat model of pressure overload. Animal protocols were approved by the Johns Hopkins Animal Care and Use Committee. A well-characterized rat model was used with modification.[14] Six-week old, male Wistar rats weighing ~100 g (Charles River Laboratories, Wilmington, Mass.) were anesthetized with 1-2% isoflurane and mechanically ventilated. Through a right thoracotomy, a 23 gauge needle was placed adjacent to the ascending aorta and a 4-O silk suture ligature was applied around both. The needle was then removed to create an immediate >70% luminal stenosis. Sham control animals underwent thoracotomy without suture placement. To investigate the effects of TGF-β, rats were administered 1 mg/kg of either a neutralizing anti-TGF-β antibody (MAB240; R&D Systems, Minneapolis, Minn.) or an IgG1 isotype control antibody (MAB005; R&D) via peritoneal injection 24 hours prior to surgery with a second dose of 0.5 mg/kg administered 48 hours after surgery. The antibody dose was based on previous studies in the rat demonstrating efficacy at inhibiting the effects of TGF-β.[15]

At sacrifice, echocardiographic measurements were obtained with a Sonos 550 Ultrasound System (Hewlett-Packard, Andover, Mass.) equipped with a 15 MHz probe (SiemansAcuson, Malvern, Pa.) using validated techniques in rodents.[16] Ventricular pressures were measured directly via cardiac puncture with a 21 gauge needle attached to a pressure monitor (SpaceLabs, Redmond, Wash.).

Atrial gene transfer. The construction of adenovirus vectors expressing human TM (AdTMh5) and no transgene (Ad-Null) have been previously described.[13] The left atrium was exposed via a left thoracotomy and 400 μL of a solution containing 20% Pluronic F-127 (Molecular Probes, Eugene, Oreg.), 0.5% trypsin, and $10^{10}$ plaque forming units/mL of the indicated adenovirus vector were directly applied to the epicardial surface of the left atrium with a camel hair paintbrush. The applied solution was allowed to gel for 10 minutes prior to closure of the thoracotomy. Five days after atrial gene transfer, banding of the ascending aorta was performed as described. The expression of recombinant human TM protein in transduced atria was assessed in tissue lysates by ELISA as described.[13]

Assessment of neurohormonal activation. At the time of sacrifice, levels of angiotensin II, atrial natriuretic peptide, and brain natriuretic peptide were determined in extracted serum using EIA kits recognizing rat peptides (Phoenix Pharmaceuticals, Belmont, Calif.) according to the manufacturer's instructions. Serum TNF-α concentrations were measured by rat TNF-α ELISA kit (BioSource, Camarillo, Calif.) according the manufacturer's instructions.

Real-Time quantitative PCR. RNA from freshly harvested tissue or cultured cells was extracted using TRIZOL Reagent (Invitrogen, Carlsbad, Calif.). Real-time quantitative PCR was performed using a 7900HT Sequence Detection System (Applied Biosystems, Foster City, Calif.). Triplicate samples were subjected to reverse transcription and real-time PCR using TaqMan One-Step RT-PCR Master Mix Reagents with gene-specific primers and probes designed by Primer Express software (Applied Biosystems) based on published nucleotide sequences (see Methods Supplement). TM gene expression was normalized to endothelial-specific RNA content by quantifying rat CD31 gene expression. TM gene expression in cultured cells and TGF-β gene expression in both tissue samples and cultured cells were normalized to 18S ribosomal RNA (TaqMan Ribosomal RNA Reagents with VIC-labeled probe; Applied Biosystems).

Western blot and immunohistochemical analyses. Western blotting was performed using anti-TM antibodies (#3381 and #2380; American Diagnostica) and an anti-CD31 antibody (M0823; Dako, Carpinteria, Calif.) as described.[13] Bands were detected by autoradiography and quantified densitometrically using UN-SCAN-IT software (Silk Scientific, Orem, Utah). Immunohistochemical analysis was performed on formalin-fixed and paraffin-embedded sections of rat left atria using antibodies against rat TM (#3381; American Diagnostica), human TGF-α latent associated peptide (EF01; R&D) and rat prolyl 4-hydroxylase (6-9H6; Acris Antibodies, Hiddenhausen, Germany) as described.[8]

In situ Protein C and thrombin activity assays. Activated protein C (APC)-generating capacity was measured on freshly-harvested whole left atria using a previously described protocol with modification.[13] The atria were washed in Hank's buffered salt solution (HBSS) then incubated in 250 μL HBSS containing 40 nmol/L human α-thrombin (Sigma-Aldrich, St. Louis, Mo.) and 1 umol/L human protein C (American Diagnostica) at 37° C. After 60 minutes, thrombin was neutralized by excess lepirudin (Berlex Laboratories, Montville, N.J.). 100 μL aliquots were incubated at room temperature with a 3-mmol/L solution of the chromogenic substrate, S-2366 (DiaPharma, West Chester, Ohio). The rate of substrate conversion was determined spectrophotometrically using a Vmax Kinetic Microplate Reader (Molecular Devices, Sunnyvale, Calif.) and the amount of protein C activation calculated by comparison to a human APC (American Diagnostica) standard curve. Bound thrombin activity on the atrial endocardial surface was measured as previously described with some modification.[13] Freshly excised whole atria were washed in HBSS, then incubated in 250 μL of substrate buffer (50 mmol/L Tris-HCl, 175 nmol/L NaCl, and 2 mmol/L CaCl2 (pH 7.8) containing 333 umol/L of the chromogenic substrate, S-2238 (DiaPharma)) at 37° C. for 30 minutes. The change in absorbance at 405 nm before and after lepirudin treatment represented thrombin-specific substrate conversion. Bound thrombin activity was then calculated by comparison to a human α-thrombin standard curve.

In vitro stretch experiments. Human atrial endocardial cells isolated in our laboratory (see Methods Supplement) and human cardiac fibroblasts purchased from Cell Applications, San Diego, Calif. of passage 2-3 were plated onto type I collagen-coated 6-well Bioflex plates (Flexcell International, Hillsborough, N.C.) and grown in either EGM-2 (endocardial cells) or FGM-2 (fibroblasts) culture media (Bio-Whittaker). When nearly confluent, cells were refreshed in basal media and subjected to 0-10% cyclic strain delivered at 1 Hz for 24 hours at 37° C. and 5% $CO_2$ hours using a FX-4000T Tension Plus System (Flexcell International). For co-culture experiments, atrial endocardial cells were grown on 24 mm diameter Transwell inserts with a 0.4 μm pore size (Corning, Corning, N.Y.) in EGM-2 medium. When confluent, the inserts were placed into the individual wells of the Bioflex plates containing cardiac fibroblasts in basal medium (FBM; BioWhittaker). The cardiac fibroblasts were then subjected to 0-10% cyclic strain at 1 Hz for 24 hours. To investigate the effects of TGF-β, 0.5 μg/mL of either a neutralizing anti-TGF-β (MAB240; R&D) or IgG1 isotype control antibody (MAB005; R&D) were added to the medium prior to stretching the fibroblasts at 10% cyclic strain delivered at 1 Hz for 24 hours.

Statistical Analysis. All data are presented as mean±SEM. Comparison between two groups is by two-tailed t tests and between multiple groups by one-way ANOVA with a Bonferroni correction for intergroup comparisons. Statistically relationships not otherwise indicated are to be assumed non-significant (p>0.05).

EXAMPLE 2

Figure 1A:
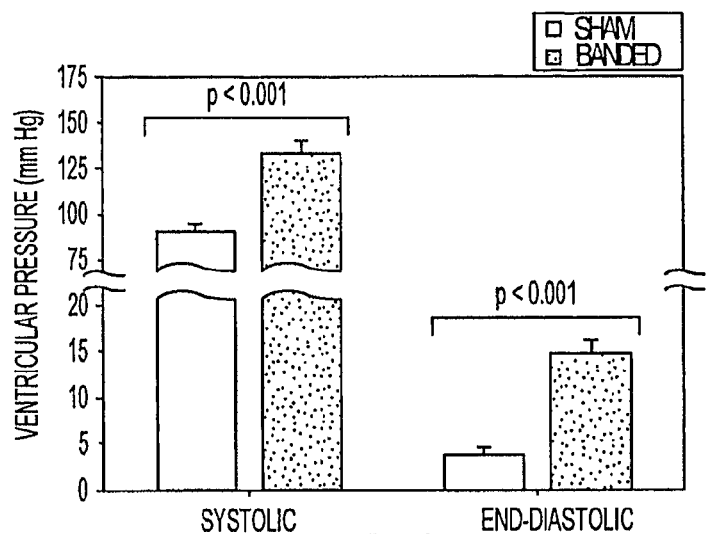
FIGS. 1A-1C. Effects of suture banding of the ascending aorta 96 hours after surgery.
Figure 1B:
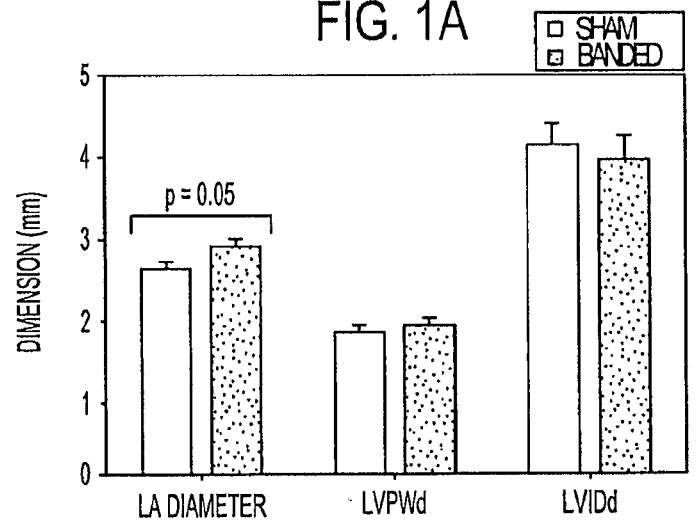
Figure 1C:
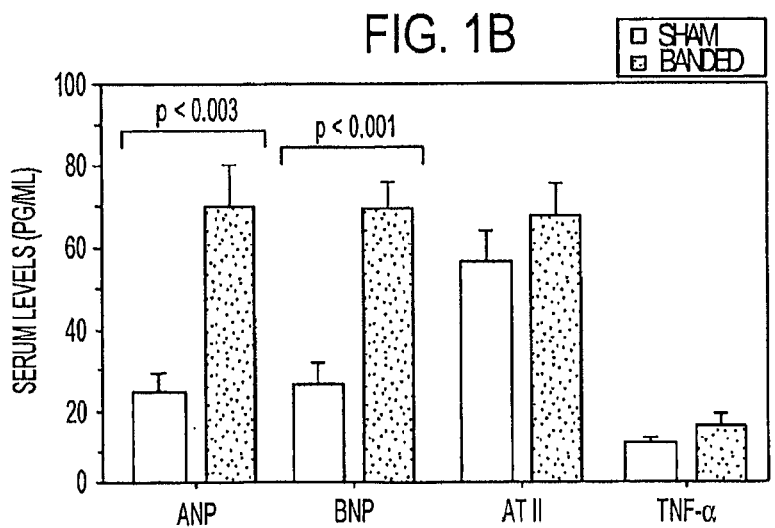

Effects of acute pressure overload on endocardial TM expression. The ascending aortae of 6 week old rats were suture banded to induce a >70% luminal constriction. Because this degree of acute increase in afterload results in pulmonary edema and death within 7 days of surgery, all hemodynamic and echocardiographic measurements were obtained 96 hours after banding. Compared to sham-operated controls, left ventricular systolic pressure increased 40% in banded animals while left ventricular diastolic pressure, equivalent to mean left atrial pressure, increased by nearly 400% (p<0.0001 for both; FIG. 1A). Ventricular wall thickness and diastolic diameter were unchanged, while left atrial diameter increased slightly (FIG. 1B). Systolic function was not depressed in this acute period, with ejection fractions rising slightly (77±9% banded versus 65±5% sham controls, p<0.01) and likely reflecting acute compensation to high afterload.[17] Serum atrial natriuretic peptide and brain natriuretic peptide levels were >3-fold higher in banded rats, consistent with the induction of heart failure, whereas angiotensin II and tumor-necrosis factor-α levels did not differ from controls (FIG. 1C).

Figure 2A:
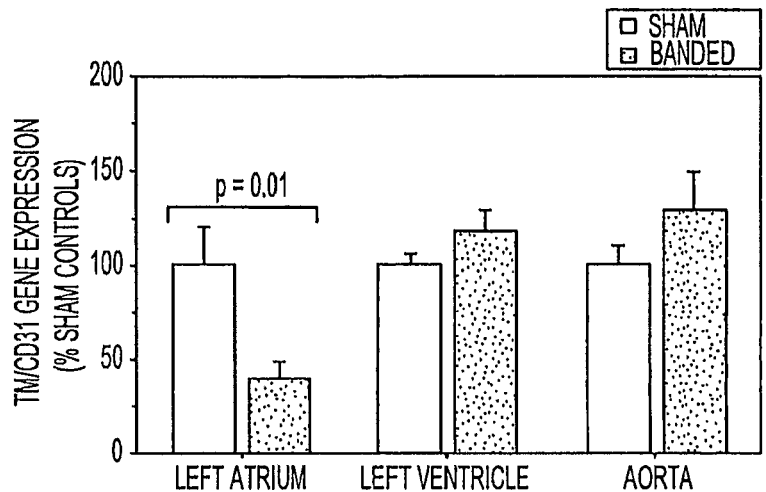
FIGS. 2A-2C. Effect of acute pressure overload on endocardial TM expression.
Figure 2B:
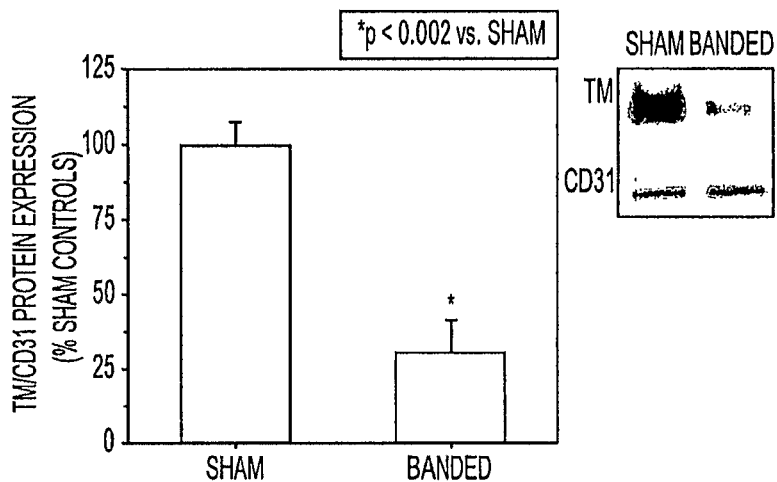
Figure 2C:

To determine the impact of acute hemodynamic changes on endocardial TM expression, tissue from the left atrium and ventricle of banded rats was subjected to quantitative PCR analysis and compared to sham controls (FIG. 2A). Aortic tissue, distal to the suture ligature, was analyzed as an additional control. Data were normalized to CD31, an endothelial-specific adhesion molecule whose expression does not change with pressure-induced cell stretch.[18] TM expression in the left atrium of banded rats declined by 60% compared to sham controls (p=0.01), whereas TM expression in the left ventricle or in the distal aorta was unchanged. Western blot analysis of left atrial tissue confirmed a 70% decline in TM expression (p<0.002; FIG. 2B). Left atrial tissue stained with an anti-mouse TM antibody verified decreased TM expression by the atrial endocardial endothelium (FIG. 2C). These data suggest that endocardial TM expression is directly modulated by changes in chamber loading, rather than by systemic factors induced by acute heart failure.

Figure 3:
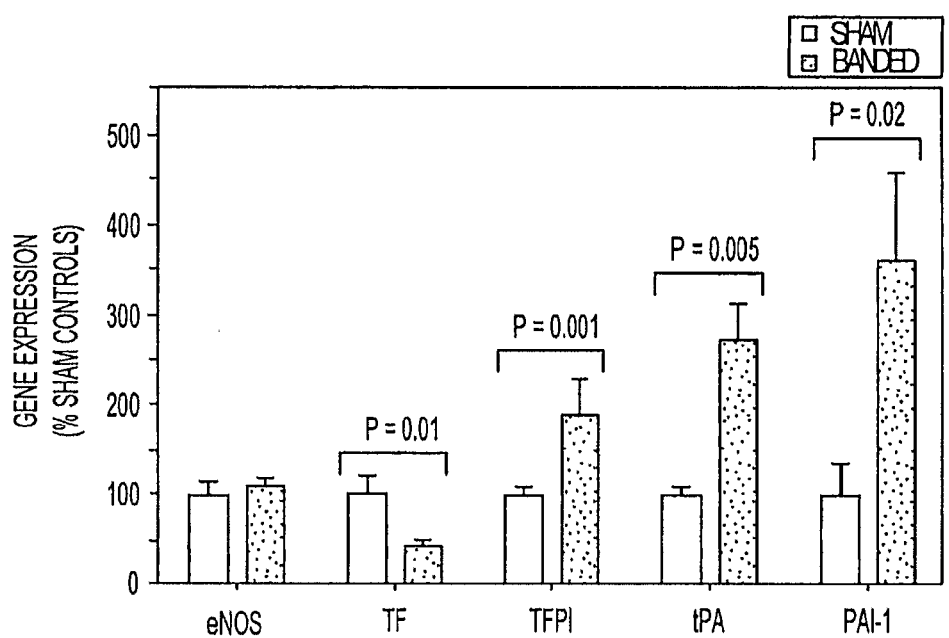
FIG. 3. Effect of acute pressure overload on the expression of molecules modulating endocardial thromboresistance. Gene expression, normalized to CD31, was determined by quantitative PCR of tissue extracts obtained from the left atrium of banded and sham rats 96 hours after surgery (n=10/group).

We also determined if acute pressure overload altered the atrial expression of other molecules known to modulate endocardial thromboresistance (FIG. 3). Aortic banding did not alter the expression of endothelial nitric oxide synthase (eNOS) but was associated with increased tissue factor pathway inhibitor (TFPI) and decreased tissue factor expression. The net effect of these changes would be expected to reduce local thrombin generation at the endocardial surface. Interestingly, banding also increased the expressions of both tissue plasminogen activator (tPA) and plasminogen activator inhibitor-1 (PAI-1).

EXAMPLE 3

Consequences of TM downregulation on endocardial thromboresistance. TM exerts its anticoagulant effect via activation of circulating protein C. Endocardial APC generating capacity was measured in resected whole left atria 96 hours after surgery. Aortic banding reduced the APC-generating capacity of the left atria of banded rats by >35% compared to sham controls (p=0.01; FIG. 4A). To determine the effect on in situ thrombin generation, the activity of thrombin bound to the atrial endocardial surface was then quantified. Thrombin generated at sites of vascular injury binds to fibrin strands within a developing clot and is protected from inactivation by circulating inhibitors. Bound thrombin activity is therefore proportional to the degree of thrombus that is present and is capable of detecting the presence of microscopic amounts of fibrin clot.[12] Bound thrombin activity in the atria of banded rats was significantly higher than in atria from sham operated controls and approached that observed in atria subjected to direct mechanical forcep injury (FIG. 4B).

Figure 8:
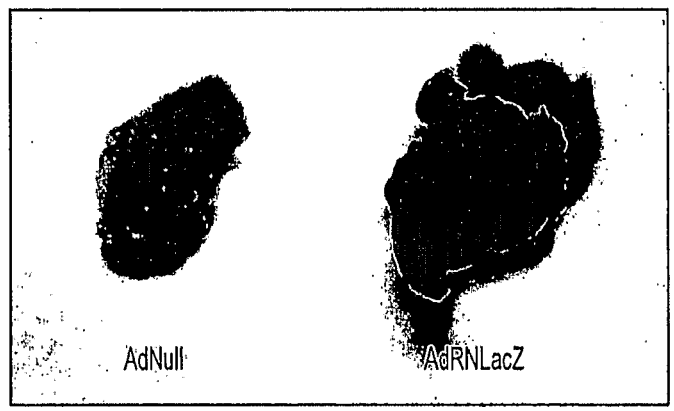
FIG. 8. Solutions of 20% poloxamer, 0.5% trypsin and $10^{10}$ plaque forming units/mL of an adenovirus vector expressing either no transgene (AdNull) or β-galactosidase (AdRN-LacZ) were applied directly to the epicardial surface of the rat left atrium. Three days after transduction, atrial tissue was resected and incubated in X-gal solution. The blue discoloration denotes β-galactosidase expression.

We then determined the effects of restoring TM expression on APC-generating capacity and bound thrombin activity. This was accomplished using a "gene painting" technique whereby solutions containing adenovirus vectors expressing either human TM (AdTM5) or no transgene (AdNull) were applied to the epicardial surfaces of the rat left atria. Previous studies in the pig revealed that this technique results in efficient transmural transduction of atrial cells, including the endocardial endothelium.[19] FIG. 8 illustrates the degree of gene transfer that can be attained with this method in the rat. Three days after transduction, protein lysates of left atrial tissue subjected to ELISA that detects only the human form of TM[13] revealed an average of 76.5±24.9 ng of human TM/mg of atrial tissue in AdTMh5-transduced atria (n=4) whereas no human TM was detected in AdNull-transduced atria (n=3; p<0.004). These results were confirmed by Western blot analysis (FIG. 4C). To verify that acute pressure overload does not attenuate transgene expression, transduced atria from suture-banded rats were assayed for the expression of both human and native rat TM by quantitative PCR 96 hours after surgery. FIG. 4D demonstrates that human TM gene expression remains robust throughout the experimental period in AdTMh5-transduced atria whereas no human TM gene expression could be detected in AdNull-transduced atria. Restoration of TM expression using adenovirus-mediated gene transfer effectively prevented the loss of APC-generating capacity induced by aortic banding (FIG. 4A) and reduced the levels of bound thrombin activity to baseline values (FIG. 4B). Taken together, these data support the concept that downregulation of endocardial TM contributes to increased local thrombin generation.

EXAMPLE 4

Figure 5A:
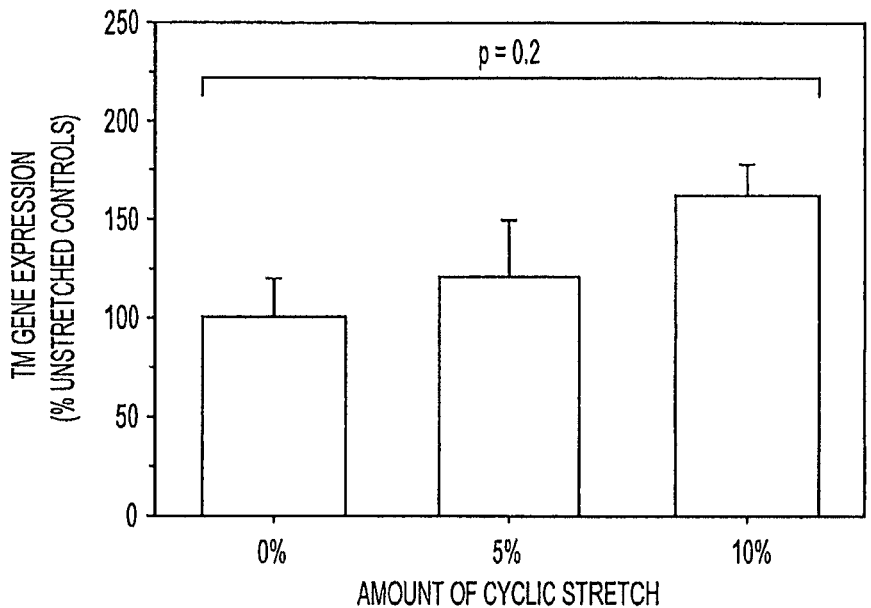
FIGS. 5A-5B. Effect of cyclic stretch on endocardial TM expression.
Figure 5B:
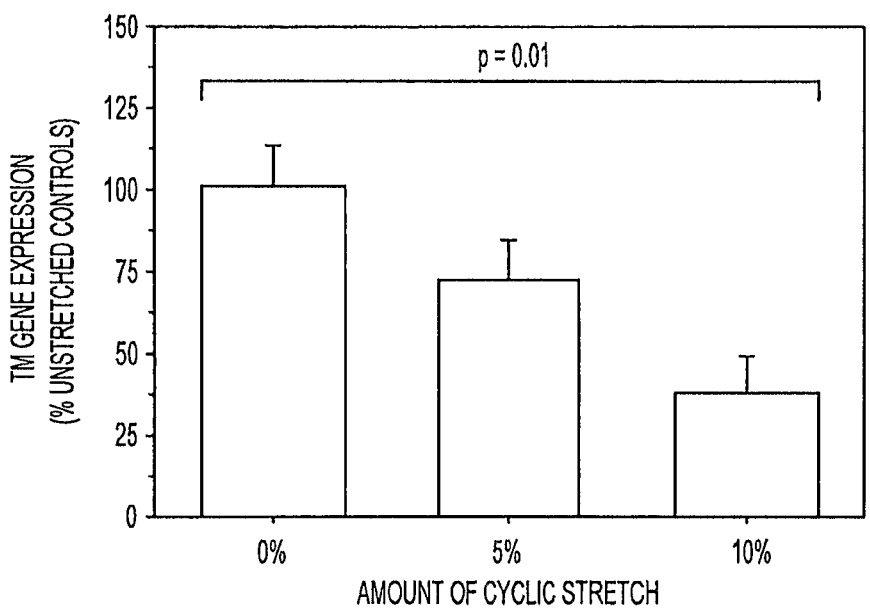

Effects of stretch on TM expression in isolated endocardial endothelial cells. We have previously shown that TM downregulation in vein segments exposed to arterial pressure results from pressure-induced vascular stretch and not from the direct effects of pressure per se.[12] To determine if stretch can directly inhibit TM gene expression, endocardial endothelial cells isolated from human right atrial appendages were grown on collagen-coated silastic membranes and subjected to increasing amounts of cyclic stretch for 24 hours. Surprisingly, cyclic stretch resulted in a trend toward increased TM gene expression (FIG. 5A). Similar results were observed in stretched endothelial cells isolated from both rabbit jugular veins and human umbilical veins (data not shown). Because endocardial endothelial cells in situ lie adjacent to cardiac connective tissue, we next tested if this interaction might influence TM expression by stretch. Human atrial endocardial cells were cultured on stationary filters suspended in the media of wells containing human cardiac fibroblast that were subjected to increasing amounts of cyclic stretch. Stretching of cardiac fibroblasts resulted in a dose-dependent decrease in TM expression in the stationary endocardial cells (FIG. 5B). Experiments substituting human aortic smooth cells for cardiac fibroblasts yielded identical results (data not shown). These results indicate that endocardial TM expression is modulated in paracrine fashion by a soluble factor released by cardiac connective tissue in response to stretch.

EXAMPLE 5

Effects of stretch on TM expression in isolated endocardial endothelial cells. We have previously shown that TM downregulation in vein segments exposed to arterial pressure results from pressure-induced vascular stretch and not from the direct effects of pressure per se.[12] To determine if stretch can directly inhibit TM gene expression, endocardial endothelial cells isolated from human right atrial appendages were grown on collagen-coated silastic membranes and subjected to increasing amounts of cyclic stretch for 24 hours. Surprisingly, cyclic stretch resulted in a trend toward increased TM gene expression (FIG. 5A). Similar results were observed in stretched endothelial cells isolated from both rabbit jugular veins and human umbilical veins (data not shown). Because endocardial endothelial cells in situ lie adjacent to cardiac connective tissue, we next tested if this interaction might influence TM expression by stretch. Human atrial endocardial cells were cultured on stationary filters suspended in the media of wells containing human cardiac fibroblast that were subjected to increasing amounts of cyclic stretch. Stretching of cardiac fibroblasts resulted in a dose-dependent decrease in TM expression in the stationary endocardial cells (FIG. 5B). Experiments substituting human aortic smooth cells for cardiac fibroblasts yielded identical results (data not shown). These results indicate that endocardial TM expression is modulated in paracrine fashion by a soluble factor released by cardiac connective tissue in response to stretch.

EXAMPLE 6

Figure 6A:
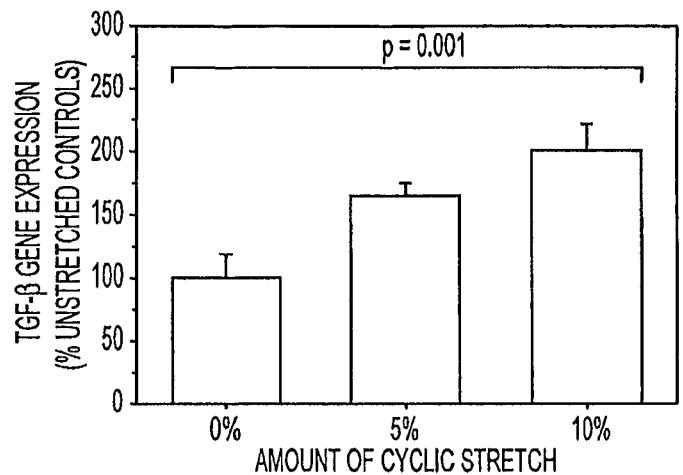
FIGS. 6A-6C. Effect of TGF-β on endocardial TM expression.
Figure 6B:
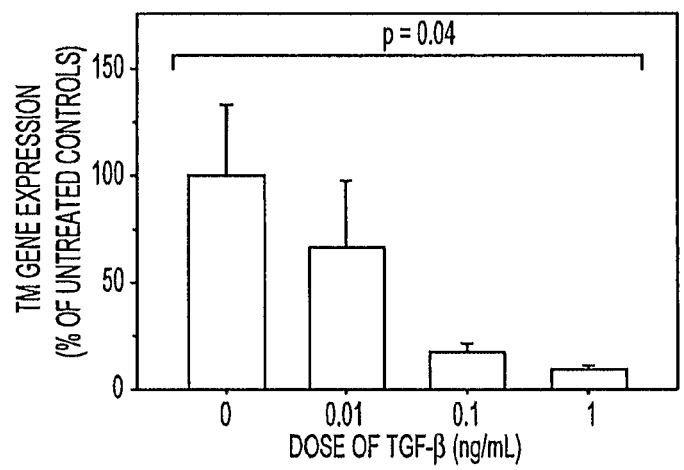
Figure 6C:
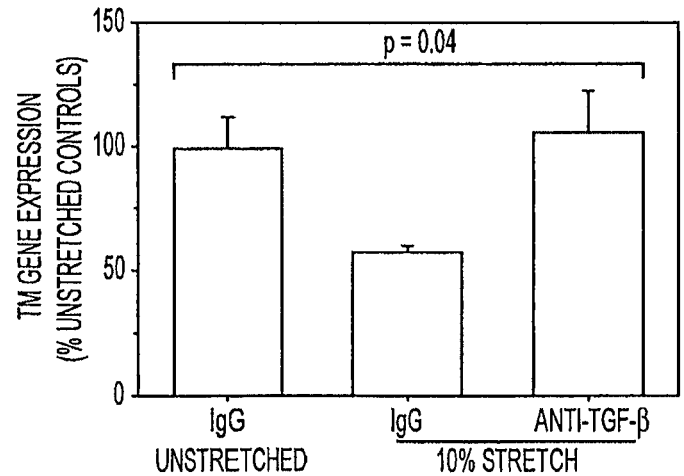

Modulation of TM expression by paracrine release of TGF-β. TGF-β is a multifunctional stretch-induced growth factor known to be intimately involved in cardiac remodeling induced by heart failure[20] and has been reported to inhibit TM protein expression in human umbilical vein endothelial cells.[21] TGF-β gene expression in cardiac fibroblasts exhibited a dose-dependent increase in response to cyclic stretch (FIG. 6A). In addition, TM gene expression in human atrial endocardial cells was inhibited in a dose-dependent manner after a 24-hour exposure to recombinant TGF-$\beta_1$ (FIG. 6B). To determine if TGF-β is the paracrine factor responsible for TM downregulation, human endocardial cells were plated on stationary filters submerged in the media of cardiac fibroblasts subjected to 10% cyclic stretch for 24 hours in the presence of a neutralizing anti-TGF-β antibody or an isotype control antibody. FIG. 6c shows that neutralization of TGF-β effectively prevented the downregulation of endocardial TM gene expression.

Figure 7A:
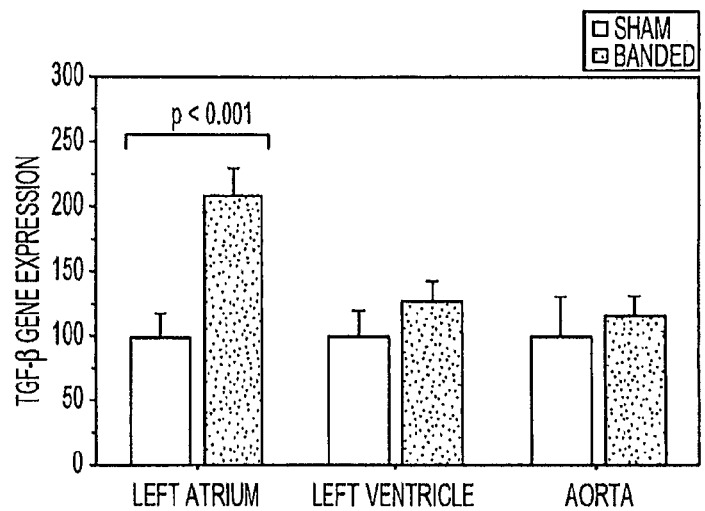
FIG. 7A-7C. Effect of TGF-β on endocardial TM expression in heart failure.
Figure 7B:
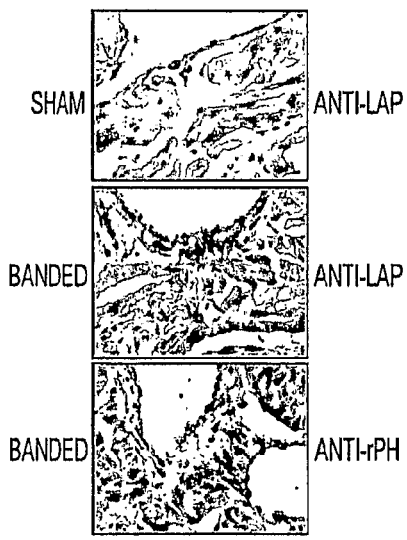
Figure 7C:
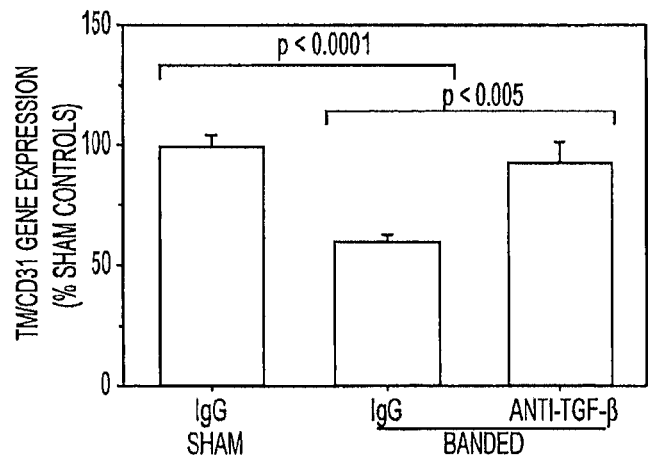

To determine if paracrine release of TGF-β is responsible for in vivo modulation of TM, we first assessed TGF-β expression in the cardiovascular tissue of rats subjected to aortic banding. Compared to sham-operated controls, TGF-β gene expression in the left atrium of banded rats increased by >200% (p<0.001), whereas there was no significant change in TGF-β expression in the left ventricle or in the distal aorta (FIG. 7a). Banding was also associated with increased TGF-β activation as evidenced by positive immunostaining for latency associated peptide (LAP), the cleaved propeptide of the TGF-β precursor molecule that remains non-covalently attached to active TGF-β. LAP staining localized predominantly to fibroblast-appearing cells in the subendocardial space that also expressed an abundance of the prolyl 4-hydroxylase, an enzyme involved in collagen synthesis (FIG. 7B). To determine if TGF-β inhibition could prevent TM downregulation, rats were administered either a neutralizing anti-TGF-β antibody or an isotype control antibody in the peri-operative period. Neutralization of TGF-β effectively prevented TM downregulation in the left atrium 96 hours after aortic banding (FIG. 7C). Importantly, there was no meaningful difference in the hemodynamic response to banding between rats administered the anti-TGF-β antibody versus the isotype control antibody (LVEDP 17.7±0.6 versus 15.8±0.2 mm Hg, respectively, p=0.02). These data confirm that the effects of pressure overload on endocardial TM expression and thromboresistance are mediated via paracrine release of TGF-β.

EXAMPLE 7

Figure 10A:
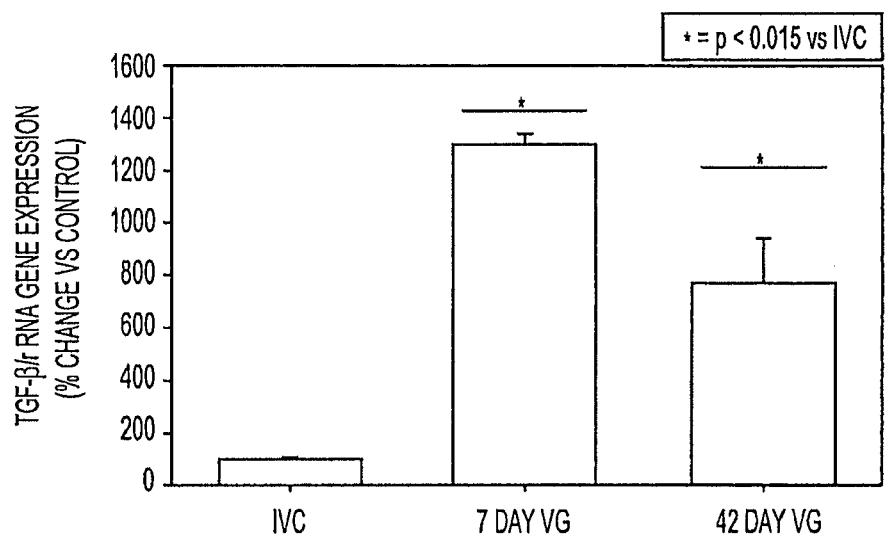
FIGS. 10A and 10B. Loss of TM expression correlates with induction of TGF-β expression in autologous vein grafts.
Figure 10B:
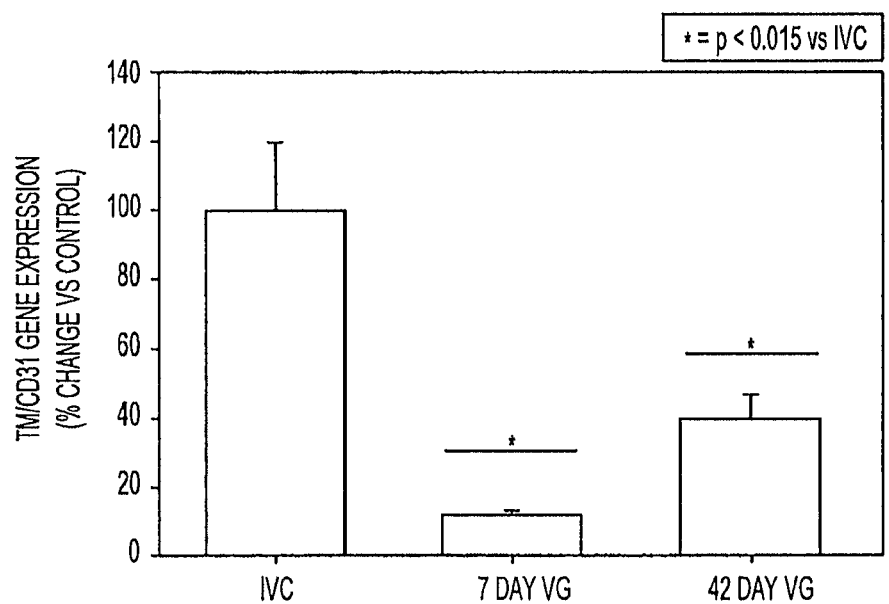

Loss of TM expression correlates with induction of TGF-β expression in autologous vein grafts. As shown in FIG. 10A, exposure to arterial pressure significantly downregulated TM gene expression seven days after vein graft (VG) implantation compared to inferior vena cava (IVC) controls. Downregulation of TM persisted six weeks after implantation. Similarly, as shown in FIG. 10B, exposure to arterial pressure markedly upregulated TGF-β gene expression seven days after VG implantation, which persisted six weeks after implantation (n=4/group).

EXAMPLE 8

Figure 11:
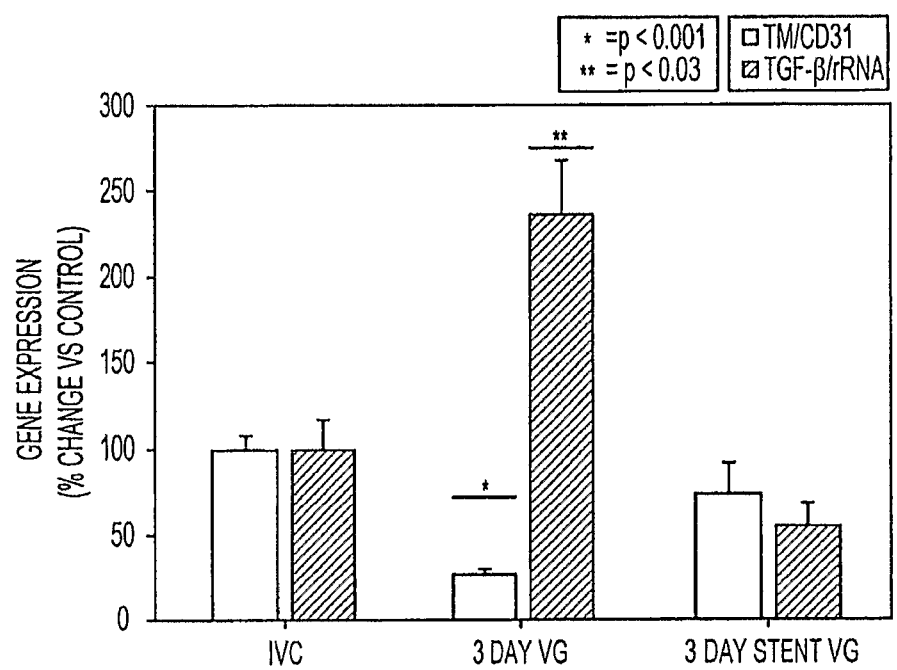
FIG. 11. Reducing wall tension prevents loss of TM and upregulation of TGF-β.

Reducing wall tension prevents loss of TM and upregulation of TGF-β. External stenting of VG prior to implantation attenuated TM downregulation and TGF-β upregulation, suggesting that pressure-induced stretch both negatively regulates TM expression and induces TGF-β expression (n=4/group). See FIG. 11.

EXAMPLE 9

Figure 12A:
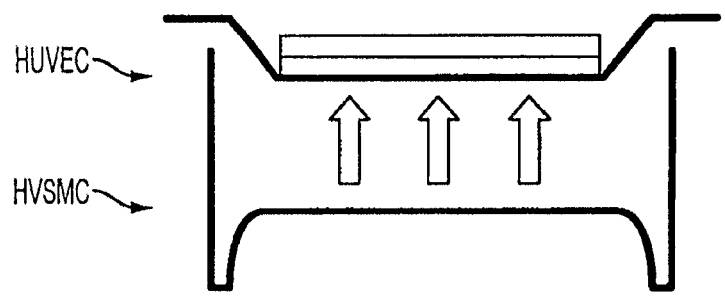
FIGS. 12A and 12B. Stretch-induced paracrine release of TGF-β by HVSMC downregulates TM expression in static HUVEC.
Figure 12B:
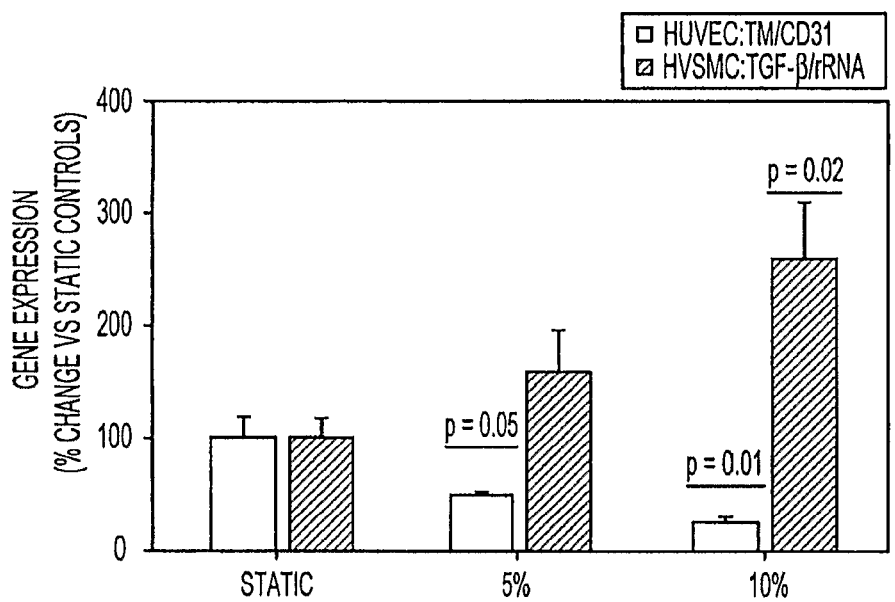

Stretch-induced paracrine release of TGF-β by HVSMC downregulates TM expression in static HUVEC. FIG. 12A. Modified FlexCell co-incubation apparatus with HUVEC grown to near-confluence on a static Transwell insert (Green) approximated 1.5 mm above human vascular smooth muscle cells (HVSMC) grown to near confluence on a Type-I collagen coated FlexCell membrane (Blue). FIG. 12B. HVSMC express increased TGF-β gene expression in a strain-dependent manner while TM gene expression is downregulated in static HUVEC when co-incubated with stretched HVSMC in a strain-dependent manner.

EXAMPLE 10

Figure 13:
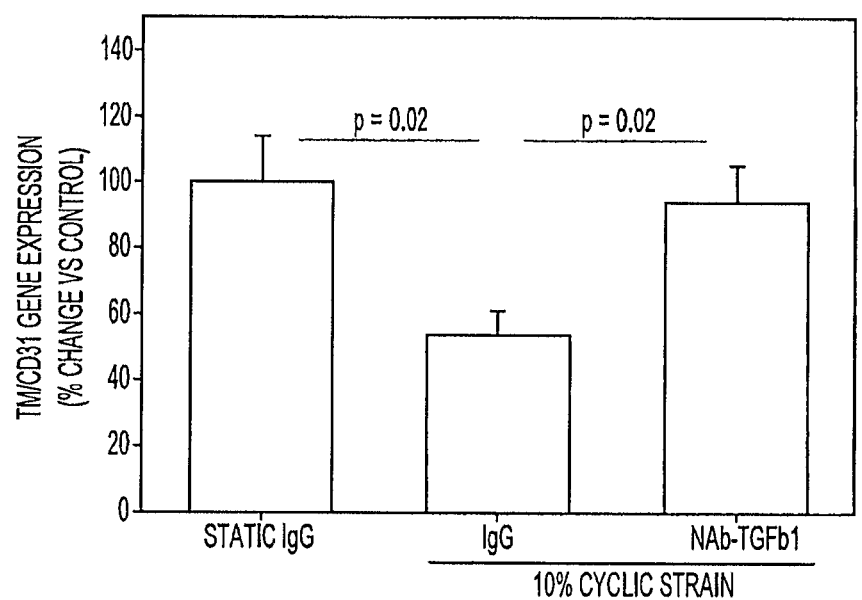
FIG. 13 Neutralization of TGF-β activity attenuates TM downregulation in vitro.

Neutralization of TGF-β activity attenuates TM downregulation in vitro. In the co-culture experimental set-up depicted in FIG. 12A, addition of a neutralizing antibody against TGFβ1 (Nab-TGFβ1; R&D MAB240) attenuated TM downregulation in static HUVEC co-incubated with stretched HVSMC compared to addition of an IgG isotype control antibody (R&D MAB005). Results are shown in FIG. 13.

EXAMPLE 11

Figure 14A:
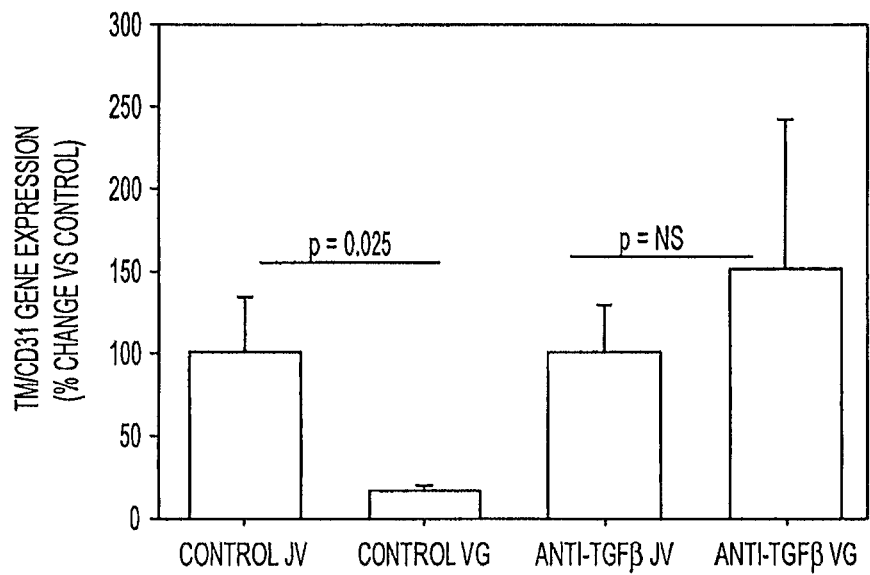
FIG. 14A and FIG. 14B. Neutralization of TGF-β activity attenuates loss of in vivo thrombomodulin expression in vein grafts.
Figure 14B:
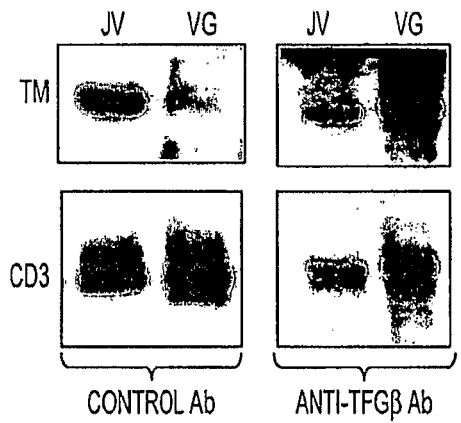

Neutralization of TGF-b activity attenuates loss of in vivo thrombomodulin expression in vein grafts. Animals were administered either a neutralizing anti-TGF-b antibody (anti-TGF Ab; Genzyme 1D11) or isotype control antibody (Control Ab; Genzyme 13C4) in the perioperative period. TM expression in vein grafts (VG) was compared to that in the ungrafted contralateral jugular vein (JV) 7 days after implantation. Neutralization of TGF-β effectively prevents down-regulation of both TM gene expression (FIG. 14A; n=6/group) and protein expression (FIG. 14B; n=4/group).

EXAMPLE 12

Figure 15A:
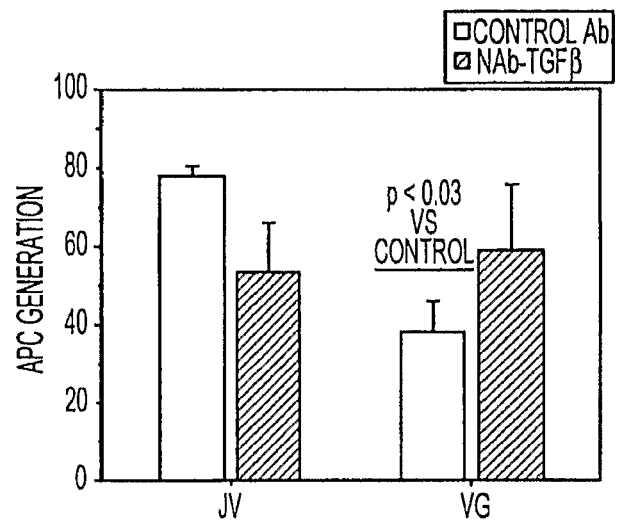
FIG. 15A and FIG. 15B Neutralization of TGF-β activity attenuates loss of TM functional activity and blunts microthrombus formation in vein grafts.
Figure 15B:
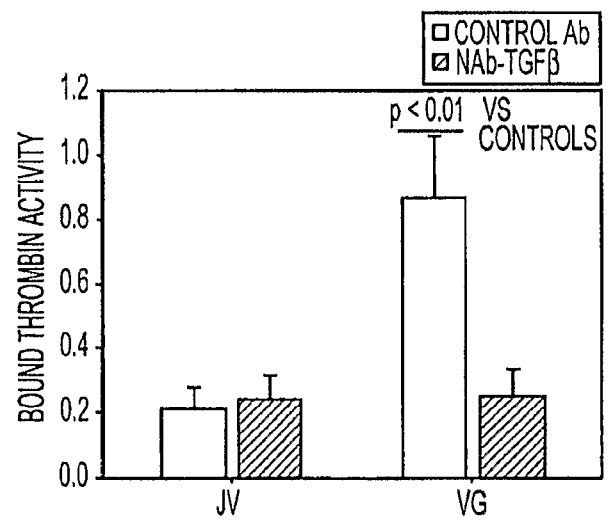

Neutralization of TGF-β activity attenuates loss of TM functional activity and blunts microthrombus formation in vein grafts. FIG. 15A) The ability of vein grafts (VG) to generate activated protein C (APC) was measured in animals (n=4/group) administered either a neutralizing anti-TGF-β antibody (Nab-TGF-β; Genzyme 1D11) or an isotype control antibody (Control Ab; Genzyme 13C4) and compared to the ungrafted contralateral jugular vein (VG) in the same animal. Neutralization of TGF-β preserves APC generating capacity of vein grafts. FIG. 15B) The amount of microthrombus formation was quantified by measuring bound thrombin activity in animals (n=4/group) administered either a neutralizing anti-TGF-β antibody (Nab-TGF-β; Genzyme 1D11) or an isotype control antibody (Control Ab; Genzyme 13C4) and compared to the ungrafted contralateral jugular vein (VG) in the same animal. Neutralization of TGF-β effectively blunts local microthrombus formation on the luminal surface of implanted vein grafts.

EXAMPLE 13

The Reductions in Graft Occlusion Rates (RIGOR) Study is an ongoing investigator-initiated multicenter observational study (PI:Rade) based at Johns Hopkins School of Medicine aimed at identifying novel risk factors for early saphenous vein graft (SVG) thrombosis after coronary artery bypass (CABG) surgery. In addition to Johns Hopkins Hospital, patients are enrolled from Christiana Hospital in Christiana, Del., Peninsula Regional Medical Center in Salisbury, Md. and Walter Reed Army Hospital in Washington, D.C. As part of the study, over 3000 clinical and laboratory data elements are collected on each patient related to their procedure and clinical course over the ensuing 2 years. Serum, plasma, DNA and urine samples are collected preoperatively, 3 days, 6 weeks and 6 months postoperatively for selected assays and the remainder stored for future analysis. Six months after CABG surgery, patients return to Johns Hopkins for non-invasive assessment of SVG patency using 64-slice multidetector CT coronary angiography (CTA).

Figure 16:
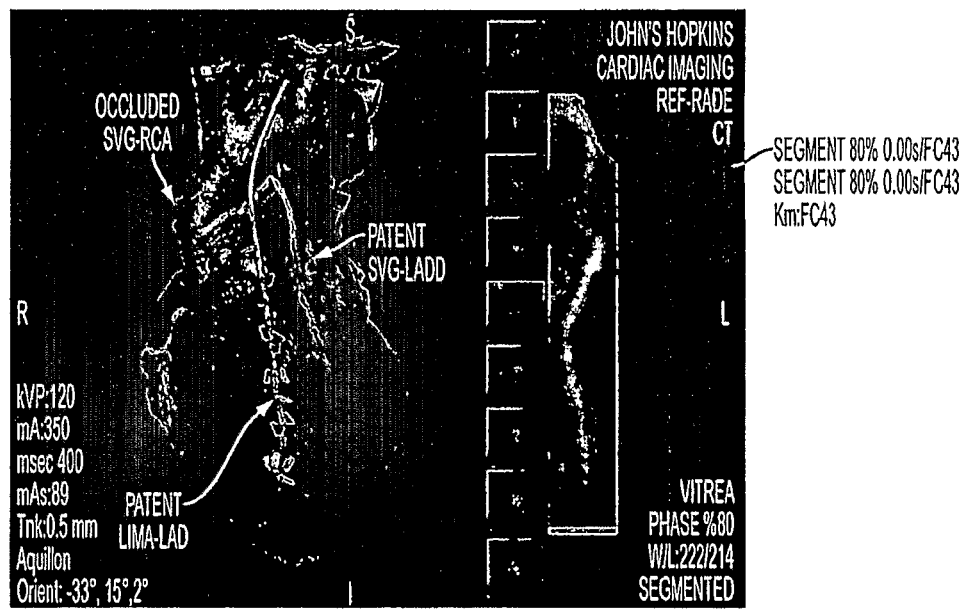
FIG. 16 is a representative 64-slice CTA of a RIGOR patient 6 months after coronary artery bypass (CABG) surgery, demonstrating the ability of 64-slice CTA to differentiate a patent from occluded saphenous vein graft (SVG). By 3-D reconstruction, the SVG to the right coronary artery (RCA) is occluded and appears as a stump. The 2-D reconstruction of the patent SVG to LADD is shown in the insert.
Figure 17:
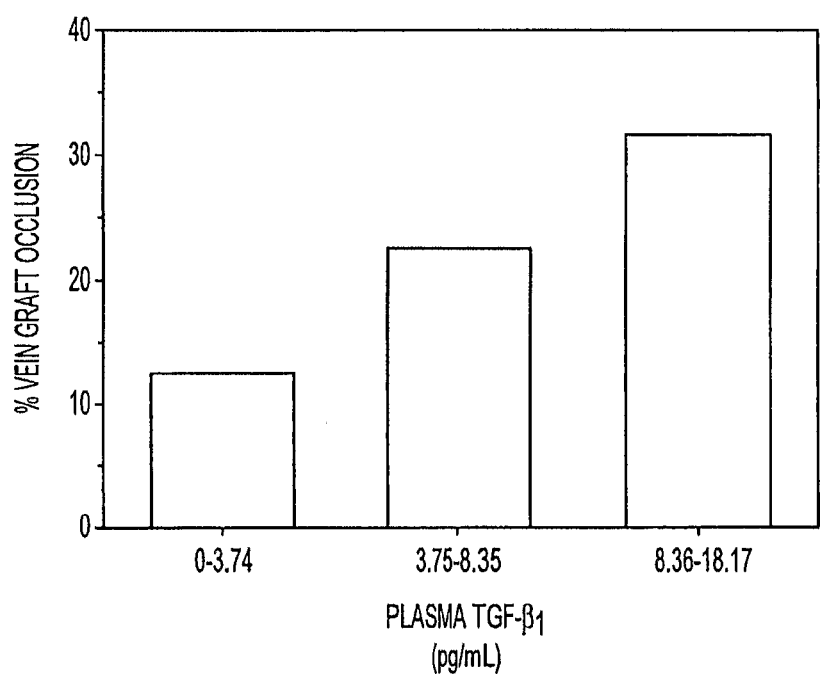
FIG. 17 shows plasma levels of TGF-β after CABG surgery versus risk of vein graft thrombosis.

As of Mar. 8, 2007 SVG patency has been assessed in 615 SVG in 291 patients. An occluded SVG is defined as having a >75% stenosis, similar to the angiographic criteria employed in the PREVENT IV trial. Of the 615 SVG grafts evaluated to date, the 6-month graft occlusion rate is 23.6% (n=145), of which <2% contained stenoses of 75-99% with the remainder being 100% occluded, consistent with vein graft thrombosis. FIG. 16 is a representative 64-slice CTA of a RIGOR patient 6 months after CABG surgery, demonstrating the ability of this technique to differentiate a patent from occluded SVG.

We have also begun to measure plasma levels of TGF-β, in patients before and after CABG surgery. Preliminary data obtained in 40 patients, reveals that patient in the highest tertile of plasma TGF-β1 levels measured 6 months after CABG surgery had twice the rate of SVG occlusion as patients in the lowest tertile. This is consistent with the concept that increased expression of TGF-β predisposes to early vein graft thrombosis.

The disclosure of each reference cited is expressly incorporated herein.

References

1. Fuster V, Gersh B J, Giuliani E R, Tajik A J, Brandenburg R O, Frye R L. The natural history of idiopathic dilated cardiomyopathy. *Am J. Cardiol.* 1981; 47:525-531.
2. Dunkman W B, Johnson G R, Carson P E, Bhat G, Farrell L, Cohn J N. Incidence of thromboembolic events in congestive heart failure. The V-HeFT VA Cooperative Studies Group. *Circulation.* 1993; 87:VI94-101.
3. Dries D L, Rosenberg Y D, Waclawiw M A, Domanski M J. Ejection fraction and risk of thromboembolic events in patients with systolic dysfunction and sinus rhythm: evidence for gender differences in the studies of left ventricular dysfunction trials. *J Am Coll Cardiol.* 1997; 29: 1074-1080.
4. Meltzer R S, Visser C A, Fuster V: Intracardiac thrombi and systemic embolization. *Ann Intern Med.* 1986; 104:689-698.
5. Gottdiener J S, McClelland R L, Marshall R, Shemanski L, Furberg C D, Kitzman D W, Cushman M, Polak J, Gardin J M, Gersh B J, Aurigemma G P, Manolio T A. Outcome of congestive heart failure in elderly persons: influence of left ventricular systolic function. The Cardiovascular Health Study. *Ann Intern Med.* 2002; 137:631-639.
6. Gibbs C R, Blann A D, Watson R D, Lip G Y. Abnormalities of hemorheological, endothelial, and platelet function in patients with chronic heart failure in sinus rhythm: effects of angiotensin-converting enzyme inhibitor and beta-blocker therapy. *Circulation.* 2001; 103:1746-1751.
7. Esmon C T. The protein C anticoagulant pathway. *Arterioscler Thromb Vasc Biol.* 1992; 12:135-145.
8. Deming C B, Kim A Y, Bian C, Regard J B, Rade J J. cDNA cloning of rabbit thrombomodulin and characterization of gene expression in cardiovascular tissue. *DNA Sequence.* 2003; 14:399-405.
9. Faust S N, Levin M, Harrison O B, Goldin R D, Lockhart M S, Kondaveeti S, Laszik Z, Esmon C T, Heyderman R S. Dysfunction of endothelial protein C activation in severe meningococcal sepsis. *N Engl J Med.* 2001; 345:408-416.
10. Richter K K, Fink L M, Hughes B M, Sung C-C, Hauer-Jensen M. Is the loss of thrombomodulin involved in the mechanism of chronicity in late radiation enteropathy? *Radiother Oncol.* 1997; 44:65-71.
11. Laszik Z G, Zhou X J, Ferrell G L, Silva F G, Esmon C T. Down-regulation of endothelial expression of endothelial cell protein C receptor and thrombomodulin in coronary atherosclerosis. *Am J. Pathol.* 2001; 159:797-802.
12. Sperry J L, Deming C B, Bian C, Walinsky P L, Kass D A, Kolodgie F D, Virmani R, Kim A Y, Rade J J. Wall tension is a potent negative regulator of in vivo thrombomodulin expression. *Circ Res.* 2003; 92:41-47.
13. Kim A Y, Walinsky P L, Kolodgie F D, Bian C, Sperry J L, Deming C B, Peck J G, Ang G B, Sohn R H, Esmon C T, Virmani R, Stuart R S, Rade J J. Early loss of thrombomodulin expression impairs vein graft thromboresistance: Implications for vein graft failure. *Circ Res.* 2002; 90:205-212.
14. Schunkert H, Dzau V J, Tang S S, Hirsch A T, Apstein C S, Lorell B H. Increased rat cardiac angiotensin converting enzyme activity and mRNA expression in pressure overload left ventricular hypertrophy. Effects on coronary resistance, contractility, and relaxation. *J Clin Invest.* 1990; 86:1913-1920.
15. Koyanagi M, Egashira K, Kubo-Inoue M, Usui M, Kitamoto S, Tomita H, Shimokawa H, Takeshita A. Role of transforming growth factor-beta1 in cardiovascular inflammatory changes induced by chronic inhibition of nitric oxide synthesis. *Hypertension.* 2000; 35:86-90.
16. Litwin S E, Katz S E, Weinberg E O, Lorell B H, Aurigemma G P, Douglas P S. Serial echocardiographic-Doppler assessment of left ventricular geometry and function in rats with pressure-overload hypertrophy. Chronic angiotensin-converting enzyme inhibition attenuates the transition to heart failure. *Circulation.* 1995; 91:2642-2654.
17. Sarnoff S J, Mitchell J H, Gilmore J P, Remensnyder J P. Homeometric autoregulation in the heart. *Circ Res.* 1960; 8:1077-1091.
18. Lauth M, Berger M M, Cattaruzza M, Hecker M. Pressure-induced upregulation of preproendothelin-1 and endothelin B receptor expression in rabbit jugular vein in situ: Implications for vein graft failure? *Arterioscler Thromb Vasc Biol.* 2000; 20:103.
19. Kikuchi K, McDonald A D, Sasano T, Donahue J K. Targeted modification of atrial electrophysiology by homogeneous transmural atrial gene transfer. *Circulation.* 2005; 111:264-270.
20. Rosenkranz S. TGF-beta1 and angiotensin networking in cardiac remodeling. *Cardiovasc Res.* 2004; 63:423-432.
21. Ohji T, Urano H, Shirahata A, Yamagishi M, Higashi K, Gotoh S, Karasaki Y. Transforming growth factor beta 1 and beta 2 induce down-modulation of thrombomodulin in human umbilical vein endothelial cells. *Thromb Haemost.* 1995; 73:812-818.
22. Maruyama I, Bell C E, Majerus P W. Thrombomodulin is found on endothelium of arteries, veins, capillaries, and lymphatics, and on synciotrophoblast of human placenta. *J Cell Biol.* 1985; 101:363-371.
23. DeBault L E, Esmon N L, Olson J R, Esmon C T. Distribution of the thrombomodulin antigen in the rabbit vasculature. *Lab Invest.* 1986; 54:172-178.
24. Blobe G C, Schiemmn W P, Lodish H F. Role of transforming growth factor beta in human disease. *N Engl J Med.* 2000; 342:1350-1358.
25. Azhar M, Schultz J J, Grupp I, Dorn G W, Meneton P, Molin D G, Gittenberger-de Groot A C, Doetschman T. Transforming growth factor beta in cardiovascular development and function. *Cytokine Growth Factor Rev.* 2003; 14:391-407.
26. Hao J, Ju H, Zhao S, Junaid A, Scammell-La Fleur T, Dixon I M. Elevation of expression of Smads 2, 3, and 4, decorin and TGF-beta in the chronic phase of myocardial infarct scar healing. *J Mol Cell Cardiol.* 1999; 31:667-678.
27. Aharinejad S, Krenn K, Paulus P, Schafer R, Zuckermann A, Grimm M, Abraham D. Differential role of TGF-beta1/bFGF and ET-1 in graft fibrosis in heart failure patients. *Am J Transplant.* 2005; 5:2185-2192.
28. Hein S. Amon E, Kostin S, Schonburg M, Elsasser A, Polyakova V, Bauer E P, Klovekorn W P, Schaper J. Progression from compensated hypertrophy to failure in the pressure-overloaded human heart: structural deterioration and compensatory mechanisms. *Circulation.* 2003; 107: 984-991.
29. Bertolino P, Deckers M, Lebrin F, ten Dijke P. Transforming growth factor-beta signal transduction in angiogenesis and vascular disorders. *Chest.* 2005; 128:585 S-590S.
30. Sandusky G, Berg D T, Richardson M A, Myers L, Grinnell B W. Modulation of thrombomodulin-dependent activation of human protein C through differential expression of endothelial Smads. *J Biol. Chem.* 2002; 277:49815-49819.
31. Hart R G, Halperin J L. Atrial fibrillation and stroke: concepts and controversies. *Stroke.* 2001; 32:803-808.
32. Yamashita T, Sekiguchi A, Iwasaki Y K, Sagara K, Hatano S, Iinuma H, Aizawa T, Fu L T. Thrombomodulin and tissue factor pathway inhibitor in endocardium of rapidly paced rat atria. *Circulation.* 2003; 108:2450-2452.
33. Yamashita T, Murakawa Y, Hayami N, Fukui E, Kasaoka Y, Inoue M, Omata M. Short-term effects of rapid pacing on mRNA level of voltage-dependent K(+) channels in rat atrium: electrical remodeling in paroxysmal atrial tachycardia. *Circulation.* 2000; 101:2007-2014.

The invention claimed is:

1. A method of prophylactically treating a patient to reduce the risk of a local thrombosis or thromboembolism, comprising:
prophylactically administering to a human patient an effective amount of a neutralizing anti-TGF-β antibody to reduce the risk of a local thrombosis or thromboembolism, wherein the human patient has a condition selected from the group consisting of: atrial fibrillation, venous insufficiency, and pulmonary hypertension.

2. The method of claim 1 wherein the patient has atrial fibrillation.

3. The method of claim 1 wherein the patient has venous insufficiency.

4. The method of claim 1 wherein the patient has pulmonary hypertension.

5. The method of claim 1 wherein the risk or incidence of cerebral thromboembolism is reduced.

6. The method of claim 1 wherein the risk or incidence of pulmonary thromboembolism is reduced.

7. The method of claim 1 wherein the risk or incidence of peripheral arterial thromboembolism is reduced.

8. A method of treating a harvested vein to reduce the risk of a local thrombosis when grafted into an artery, comprising:
prophylactically treating the harvested vein with an effective amount of a neutralizing anti-TGF-β antibody, whereby the incidence of vein graft failure due to local thrombosis is reduced.

9. The method of claim 8 wherein the vein graft is subsequently grafted in an artery.

10. The method of claim 9 wherein the artery is a coronary artery.

11. The method of claim 9 wherein the artery is a peripheral artery.

12. The method of claim 8 further, comprising:
monitoring the patency of the treated vein within 180 days after it has been grafted in an artery of a patient to determine early graft occlusion due to thrombus formation.

13. A method of prophylactically treating a patient to reduce the risk of a local thrombosis in a vein grafted into an artery, comprising:
prophylactically administering to a patient prior to, during, or subsequent to receiving a vein graft into an artery, an effective amount of a neutralizing anti-TGF-β antibody, whereby the incidence of vein graft failure due to local thrombosis is reduced.

14. The method of claim 8 or 13 wherein the harvested vein or vein graft is a saphenous vein segment.

15. The method of claim 13 further, comprising:
monitoring the patency of the treated vein within 180 days after it has been grafted in an artery of a patient to determine early graft occlusion due to thrombus formation.

16. The method of claim 12 or 15 wherein the monitoring is performed non-invasively.

17. The method of claim 12 or 15 wherein the step of monitoring determines whether complete occlusion of the treated vein has occurred.

18. The method of claim 12 or 15 wherein the step of monitoring determines whether occlusion from one anastomosis to another has occurred.

19. A method to reduce the risk or incidence of a local thrombus or thromboembolism, comprising:
prophylactically administering a pharmaceutically effective amount of a neutralizing anti-TGF-β antibody to a human patient at risk of thrombus formation or thromboembolism, whereby the risk or incidence of thrombus formation is reduced, wherein the human patient is selected from the group consisting of: one subject to abnormal pressure-induced stretch, one at risk of cerebral thromboembolism, one at risk of pulmonary thromboembolism, and one at risk of peripheral arterial thromboembolism.

20. The method of claim 19 wherein the human patient is subject to abnormal pressure-induced stretch.

21. The method of claim 19 wherein the human patient is at risk of cerebral thromboembolism.

22. The method of claim 19 wherein the human patient is at risk of pulmonary thromboembolism.

23. The method of claim 19 wherein the human patient is at risk of peripheral arterial thromboembolism.

* * * * *

UNITED STATES PATENT AND TRADEMARK OFFICE
CERTIFICATE OF CORRECTION

PATENT NO.        : 8,454,952 B2                                          Page 1 of 1
APPLICATION NO. : 12/282769
DATED             : June 4, 2013
INVENTOR(S)       : Rade et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1167 days.

Signed and Sealed this
Eighth Day of September, 2015

Michelle K. Lee
*Director of the United States Patent and Trademark Office*